US009650368B2

(12) United States Patent
Cutshall et al.

(10) Patent No.: US 9,650,368 B2
(45) Date of Patent: *May 16, 2017

(54) PROCESSES AND INTERMEDIATES FOR THE PREPARATION OF A PDE10 INHIBITOR

(71) Applicant: Omeros Corporation, Seattle, WA (US)

(72) Inventors: Neil S. Cutshall, Snohomish, WA (US); Jennifer Lynn Gage, Kenmore, WA (US); Thomas L. Little, Seattle, WA (US); Wayne Douglas Luke, Lafayette, IN (US); Elisabeth C. A. Brot, Albany, NY (US); Marco Jonas, Cohoes, NY (US); Michael James McDermott, Clifton Park, NY (US); Karl E. Reineke, Niskayuna, NY (US)

(73) Assignee: Omeros Corporation, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/696,287

(22) Filed: Apr. 24, 2015

(65) Prior Publication Data

US 2016/0024069 A1 Jan. 28, 2016

Related U.S. Application Data

(60) Provisional application No. 61/985,400, filed on Apr. 28, 2014.

(51) Int. Cl.
*C07D 417/10* (2006.01)
*C07D 413/10* (2006.01)
*C07F 3/02* (2006.01)
*C07D 285/12* (2006.01)

(52) U.S. Cl.
CPC ......... *C07D 417/10* (2013.01); *C07D 285/12* (2013.01); *C07D 413/10* (2013.01); *C07F 3/02* (2013.01)

(58) Field of Classification Search
CPC ........ C07D 417/10; C07D 413/10; C07F 3/02
See application file for complete search history.

(56) References Cited

U.S. PATENT DOCUMENTS

| | | | |
|---|---|---|---|
| 5,693,652 A | 12/1997 | Takase et al. | |
| 6,177,154 B1 | 1/2001 | Matsui et al. | |
| 6,197,901 B1 | 3/2001 | Rohde et al. | |
| 6,403,805 B1 | 6/2002 | Freyne et al. | |
| 7,053,192 B2 | 5/2006 | Li et al. | |
| 7,129,238 B2 | 10/2006 | Banner et al. | |
| 7,449,486 B2 | 11/2008 | Hans et al. | |
| 7,786,139 B2 | 8/2010 | Bergmann et al. | |
| 8,278,327 B2 | 10/2012 | Bergmann et al. | |
| 8,343,970 B2 | 1/2013 | Cutshall et al. | |
| 8,377,930 B2 | 2/2013 | Cutshall et al. | |
| 8,685,975 B2 | 4/2014 | Cutshall et al. | |
| 2003/0032579 A1 | 2/2003 | Lebel et al. | |
| 2005/0135999 A1 | 6/2005 | Elomari et al. | |
| 2006/0074102 A1 | 4/2006 | Cusack et al. | |
| 2006/0128695 A1 | 6/2006 | Bourguignon et al. | |
| 2007/0032435 A1 | 2/2007 | Alani et al. | |
| 2007/0032531 A1 | 2/2007 | Smith et al. | |
| 2007/0249544 A1 | 10/2007 | Himmelsbach et al. | |
| 2008/0004448 A1 | 1/2008 | Wayne et al. | |
| 2008/0089835 A1 | 4/2008 | Burton | |
| 2008/0090834 A1 | 4/2008 | Hoover et al. | |
| 2008/0103186 A1 | 5/2008 | Glover et al. | |
| 2008/0139569 A1 | 6/2008 | Rocco et al. | |
| 2008/0300240 A1 | 12/2008 | Bergmann et al. | |
| 2008/0319024 A1 | 12/2008 | Greil et al. | |
| 2009/0069281 A1 | 3/2009 | Austad et al. | |
| 2009/0124652 A1 | 5/2009 | Ach et al. | |
| 2009/0137794 A1 | 5/2009 | Mendez et al. | |
| 2009/0176829 A1 | 7/2009 | Verhoest et al. | |
| 2009/0176983 A1 | 7/2009 | Dova et al. | |
| 2009/0203705 A1 | 8/2009 | Biagetti et al. | |
| 2009/0221586 A1 | 9/2009 | Okada et al. | |
| 2009/0239946 A1 | 9/2009 | McKeown et al. | |
| 2010/0021539 A1 | 1/2010 | Kowalski et al. | |
| 2010/0035872 A1 | 2/2010 | Cutshall et al. | |
| 2010/0035887 A1 | 2/2010 | Ricciardi | |
| 2011/0021509 A1 | 1/2011 | Bergmann et al. | |
| 2011/0224202 A1 | 9/2011 | Cutshall et al. | |
| 2013/0158081 A1 | 6/2013 | Almstead et al. | |

(Continued)

FOREIGN PATENT DOCUMENTS

DE 43 23 192 A1 1/1995
DE 43 25 846 C1 1/1995
(Continued)

OTHER PUBLICATIONS

Ex Parte Takao, Appeal 2010-010445, U.S. Appl. No. 10/693,315, decision issued Aug. 5, 2011.*
Background Information for the ACPS Meeting, "Scientific Considerations of Polymorphism in Pharmaceutical Solids: Abbreviated New Drug Applications," *ACPS Meeting* Oct. 2002, http://www.fda.gov/ohrms/dockets/ac/02/briefing/3900B1_04_polymorphism.htm, Jan. 25, 2006, 5 pages.
Okamoto et al., "Chiral HPLC for efficient resolution of enantiomers," *Chem. Soc. Rev.* 37:2593-2608, 2008.
Rodriguez-Spong et al., "General principles of pharmaceutical solid polymorphism: a supramolecular perspective," *Advanced Drug Delivery Reviews* 56:241-274, 2004.
Aggarwal et al., "A Novel One-Pot Method for the Preparation of Pyrazoles by 1,3-Dipolar Cycloadditions of Diazo Compounds Generated in Situ," *J. Org. Chem.* 68(13):5381-5383, 2003.

(Continued)

*Primary Examiner* — Matthew Coughlin
(74) *Attorney, Agent, or Firm* — Seed IP Law Group LLP

(57) ABSTRACT

The present invention is directed to an improved process for the preparation of compounds of Formula (II) and Formula (III), which are useful in the inhibition of PDE10. In particular, the present invention is directed to an improved process for the preparation of 1-(5-(4-chloro-3,5-dimethoxyphenyl)furan-2-yl)-2-ethoxy-2-(4-(5-methyl-1,3,4-thiadiazol-2-yl)phenyl)ethanone, which is useful in the inhibition of PDE10.

77 Claims, No Drawings

(56) References Cited

U.S. PATENT DOCUMENTS

| | | |
|---|---|---|
| 2013/0196994 A1 | 8/2013 | Cutshall et al. |
| 2014/0228581 A1 | 8/2014 | Cutshall et al. |

FOREIGN PATENT DOCUMENTS

| | | |
|---|---|---|
| DE | 43 43 286 A1 | 6/1995 |
| EP | 0 672 880 A1 | 9/1995 |
| EP | 1 568 691 A1 | 8/2005 |
| WO | 92/01679 A1 | 2/1992 |
| WO | 94/12461 A1 | 6/1994 |
| WO | 96/00218 A1 | 1/1996 |
| WO | 96/15096 A1 | 5/1996 |
| WO | 96/31485 A1 | 10/1996 |
| WO | 96/31486 A1 | 10/1996 |
| WO | 96/41609 A2 | 12/1996 |
| WO | 97/27190 A1 | 7/1997 |
| WO | 98/08830 A1 | 3/1998 |
| WO | 99/45914 A1 | 9/1999 |
| WO | 00/34254 A1 | 6/2000 |
| WO | 00/55139 A2 | 9/2000 |
| WO | 01/41807 A2 | 6/2001 |
| WO | 01/44226 A1 | 6/2001 |
| WO | 01/96334 A2 | 12/2001 |
| WO | 2004/011410 A1 | 2/2004 |
| WO | 2004/033652 A2 | 4/2004 |
| WO | 2004/058254 A1 | 7/2004 |
| WO | 2004/071509 A1 | 8/2004 |
| WO | 2004/094411 A1 | 11/2004 |
| WO | 2005/103022 A1 | 11/2005 |
| WO | 2006/072828 A2 | 7/2006 |
| WO | 2006/084186 A2 | 8/2006 |
| WO | 2006/116355 A1 | 11/2006 |
| WO | 2007/058338 A2 | 5/2007 |
| WO | 2007/073299 A1 | 6/2007 |
| WO | 2008/031014 A1 | 3/2008 |
| WO | 2008/040669 A2 | 4/2008 |
| WO | 2008/064342 A2 | 5/2008 |
| WO | 2009/010156 A2 | 1/2009 |
| WO | 2009/049022 A1 | 4/2009 |
| WO | 2009/143178 A2 | 11/2009 |
| WO | 2009/152825 A1 | 12/2009 |
| WO | 2010/017236 A1 | 2/2010 |
| WO | 2011/112828 A1 | 9/2011 |

OTHER PUBLICATIONS

Enders et al., "N-heterocyclic carbene catalysed asymmetric cross-benzoin reactions of heteroaromatic aldehydes with trifluoromethyl ketones," *Chem. Commun.* 46(34):6282-6284, 2010.

Fujishige et al., "Cloning and Characterization of a Novel Human Phosphodiesterase That Hydrolyzes Both cAMP and cGMP (PDE10A)," *The Journal of Biological Chemistry* 274(26):18438-18445, 1999.

Good et al., "The Synthesis of Oxazolo[3,2-a]pyridinium Salts," *J. Chem. Soc.* 14:1938-45, 1970.

Hashmi et al., "Bisphenols from Furfurals by Organocatalysis and Gold Catalysis," *Synlett* 11:1747-1752, 2007.

Hashmi et al., "Gold Catalysis: Desymmetrization in the Furan—Yne Reaction," *Synthesis* 13:2297-2307, 2010.

Kamitori et al., "Convenient Synthesis of 5-Trifluoromethyl-3-Oxazolines and 5-Trifluoromethyloxazoles," *Heterocycles* 34(5):1047-1054, 1992.

Lee et al., "Discotic liquid crystalline materials for potential non-linear optical applications: synthesis and liquid crystalline behavior of 1,3,5-triphenyl-2,4,6-triazine derivatives containing achiral and chiral alkyl chains at the periphery," *Tetrahedron Letters* 45:1019-1022, 2004.

Loughney et al., "Isolation and characterization of PDE10A, a novel human 3", 5"-cyclic nucleotide phosphodiesterase," *Gene* 234:109-117, 1999.

Lugnier, C., "Cyclic nucleotide phosphodiesterase (PDE) superfamily: A new target for the development of specific therapeutic agents," *Pharmacology & Therapeutics* 109(3):366-398, 2006.

Olin et al., "Synthesis of 4-Phenylthiazole-2-Methanol and Some of Its Derivatives. VIII," *J [Am] Chem Soc* 53:1470-1473, Apr. 6, 1931.

Pirrung et al., "Multicomponent Reactions of Convertible Isonitriles," *J Org. Chem.* 74(11):4110-4117, 2009.

Soderling et al., "Isolation and characterization of a dual-substrate phosphodiesterase gene family: PDE10A," *Proc. Natl. Acad. Sci. USA* 96:7071-7076, Jun. 1999.

Soderling et al., "Regulation of cAMP and cGMP signaling: new phosphodiesterases and new functions," *Current Opinion in Cell biology* 12:174-179, 2000.

Tanaka et al., "Inhibitors of Acyl-CoA:Cholesterol O-Acyltransferase. 2. Identification and Structure—Activity Relationships of a Novel Series of N-Alkyl-N-(heteroaryl-substituted benzyl)-N-arylureas," *J Med. Chem.* 41(13):2390-2410, 1998.

Thompson et al., "Multiple Cyclic Nucleotide Phosphodiesterase Activities from Rat Brain," *Biochemistry* 10(2):311-316, 1971.

Wilson et al., "Emerging Biology of PDE10A," *Current Pharmaceutical Design* 21:1-11, 2015.

Zafrani et al, "Diethyl bromodifluoromethylphosphonate: a highly efficient and environmentally benign difluorocarbene precursor," *Tetrahedron* 65:5278-5283, 2009.

PCT International Search Report for International Application No. PCT/US11/27927, mailed Apr. 29, 2011 (3 pages).

PCT Written Opinion of the International Searching Authority for International Application No. PCT/US/27927, mailed Apr. 29, 2011 (8 pages).

International Search Report and Written Opinion mailed Jul. 21, 2015, for International Application No. PCT/US2015/027645, 17 pages.

International Search Report and Written Opinion mailed Jul. 13, 2015, for International Application No. PCT/US2015/027647, 17 pages.

\* cited by examiner

PROCESSES AND INTERMEDIATES FOR THE PREPARATION OF A PDE10 INHIBITOR

CROSS-REFERENCE TO RELATED APPLICATION

This application claims the benefit under 35 U.S.C. §119(e) of U.S. Provisional Patent Application No. 61/985,400, filed Apr. 28, 2014. The foregoing application is incorporated herein by reference in its entirety.

BACKGROUND

Technical Field

This invention is directed to an improved process for the preparation of compounds of Formula (I), which are useful as PDE10 inhibitors. In particular, the present invention is directed to an improved process for the preparation of 1-(5-(4-chloro-3,5-dimethoxyphenyl)furan-2-yl)-2-ethoxy-2-(4-(5-methyl-1,3,4-thiadiazol-2-yl)phenyl)ethanone (Compound 1001), which is useful as a PDE10 inhibitor.

Description of the Related Art

Compounds of Formula (I) are known and potent inhibitors of PDE10:

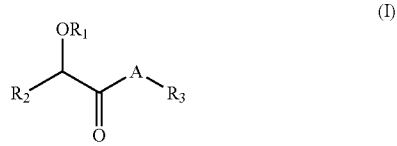

wherein:

A is:

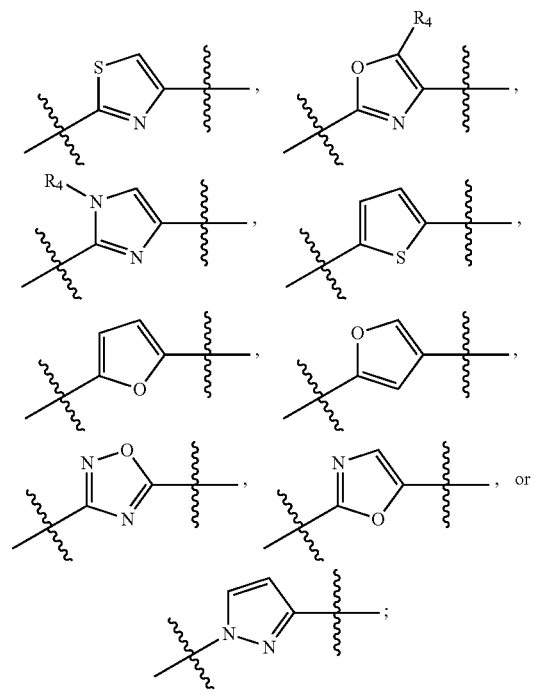

$R_1$ is $C_{1-6}$alkyl, $C_{1-6}$haloalkyl, $C_{1-6}$aralkyl, aryl, —$(CH_2)_nO(CH_2)_mCH_3$ or —$(CH_2)_nN(CH_3)_2$;

$R_2$ is (i) substituted or unsubstituted aryl or (ii) substituted or unsubstituted heterocyclyl;

$R_3$ is substituted or unsubstituted aryl;

$R_4$ is hydrogen, $C_{1-6}$alkyl or $C_{1-6}$haloalkyl;

n is 1, 2, 3, 4, 5 or 6; and m is 0, 1, 2, 3, 4, 5 or 6.

Compounds of Formula (II) are known and potent inhibitors of PDE10:

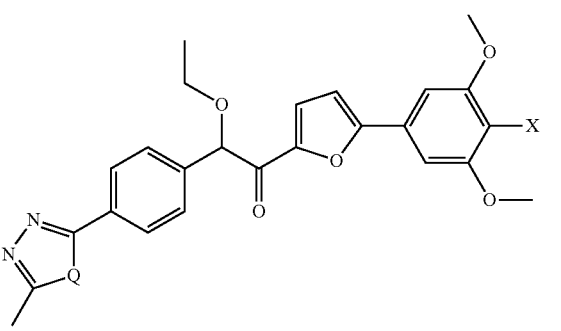

wherein:

Q is S or O; and

X is Cl or Br.

The compounds having the structure of Formula (I), Formula (II), Formula (III) and Compound 1001 fall within the scope of PDE10 inhibitors disclosed in International PCT Application Publication No. WO 2011/112828. Compound 1001 (1-(5-(4-chloro-3,5-dimethoxyphenyl)furan-2-yl)-2-ethoxy-2-(4-(5-methyl-1,3,4-thiadiazol-2-yl)phenyl)ethanone) is specifically disclosed as compound no. 65-10; Compound 1002 (1-(5-(4-bromo-3,5-dimethoxyphenyl)furan-2-yl)-2-ethoxy-2-(4-(5-methyl-1,3,4-oxadiazol-2-yl)phenyl)ethanone) is specifically disclosed as compound no. 47-1; and Compound 1003 (1-(5-(4-chloro-3,5-dimethoxyphenyl)furan-2-yl)-2-ethoxy-2-(4-(5-methyl-1,3,4-oxadiazol-2-yl)phenyl)ethanone) is specifically disclosed as compound no. 63-1 in International PCT Application No. WO 2011/112828. The compounds having the structure of Formula (I), Formula (II), and compounds 1001-1003 can be prepared according to the general procedures found in International PCT Application Publication No. WO 2011/112828, which are herein incorporated by reference.

The compounds of Formula (II) and Compound 1001 in particular have a complex structure and their synthesis is very challenging. Known synthetic methods face practical limitations and are not economical for large-scale production. There is a need for efficient manufacture of the compounds of Formula (II) and Compound 1001, in particular, with a minimum number of steps, good chemical purity, and sufficient overall yield. Known methods for production of the compounds of Formula (II) and Compound 1001, in particular, have limited yield. The present invention fulfills these needs and provides further related advantages.

BRIEF SUMMARY

The present invention is directed to a synthetic process for preparing compounds of Formula (II), in particular, Compounds 1001-1003, using the synthetic steps described herein. The present invention is also directed to particular individual steps of this process and particular individual intermediates used in this process.

In one embodiment, a process is provided to prepare a compound of Formula (II):
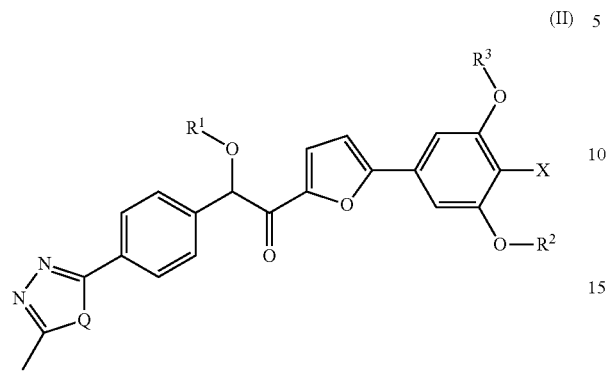
wherein
Q is S or O,
X is Cl or Br, and
$R^1$, $R^2$, and $R^3$ are each independently $C_{(1-6)}$alkyl, according to the following General Scheme (I):
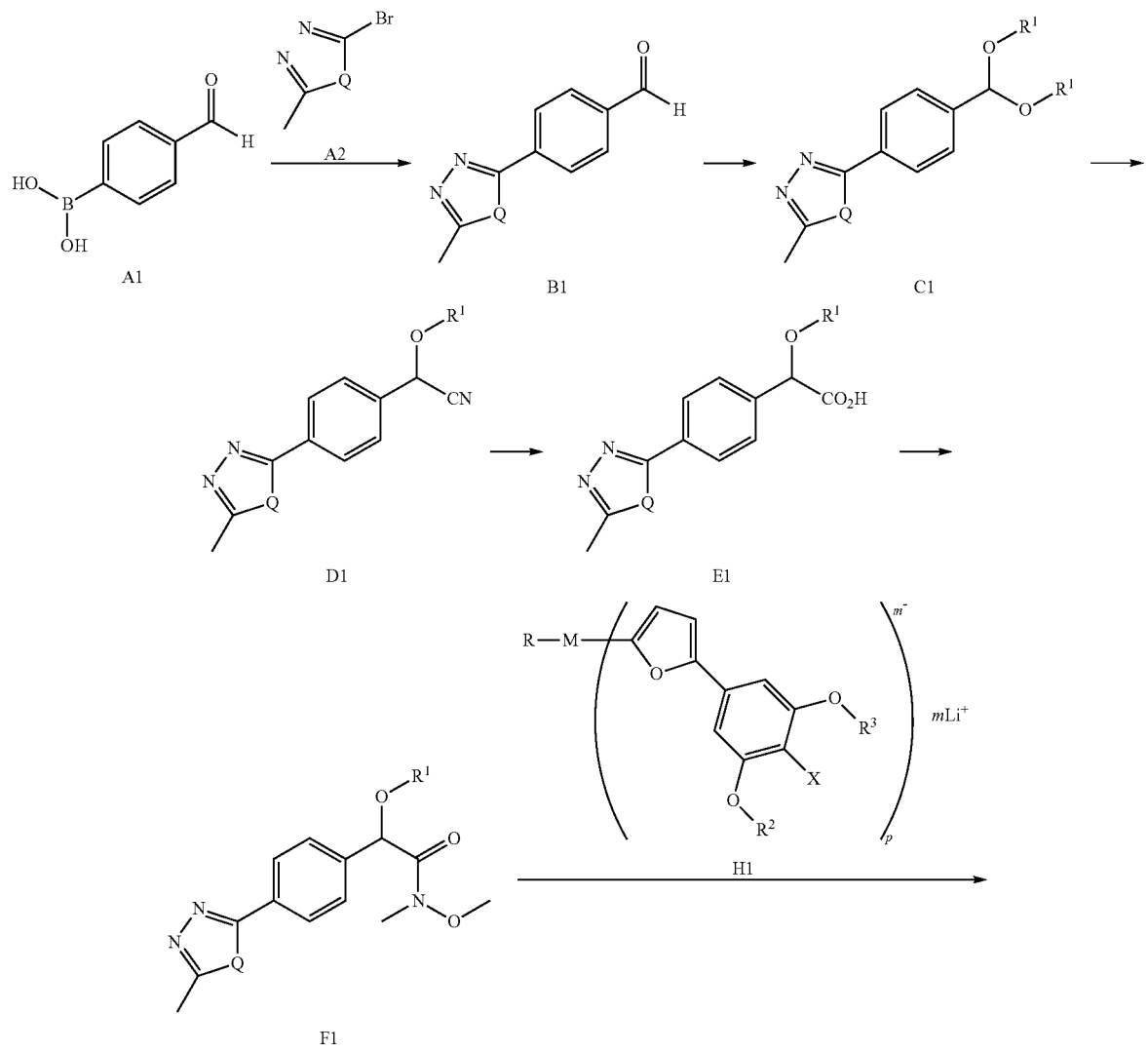

-continued

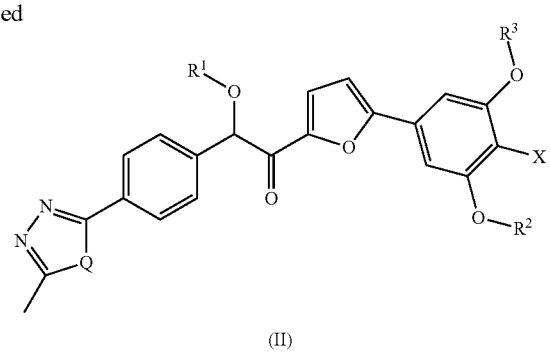

(II)

which process comprises:
- converting boronic acid A1 to carbaldehyde B1 through activation of the boronic acid with an activating reactant A2;
- converting carbaldehyde B1 to acetal C1 under acid catalysis with a suitable source of orthoformate;
- converting acetal C1 to nitrile D1 through catalyzed cyanation with a metal catalyst and a cyanide source;
- hydrolyzing D1 with a suitable acid to give carboxylic acid E1;
- converting carboxylic acid E1 to amide F1 with a suitable base, a suitable coupling reagent, and a source amine;
- converting amide F1 to a compound of Formula (II) with an anionic coupling reagent having structure H1, wherein
  - M is a Group I metal, a Group II metal, Cu, or Zn;
  - R, $R^2$, and $R^3$ are each independently $C_{(1-6)}$alkyl;
  - m is 1, 2, 3, or 4;
  - p is 1, 2, 3, or 4; and
- optionally converting the compound of Formula (II) to a salt.

Another aspect of the invention provides a process to prepare a compound of Formula H1:

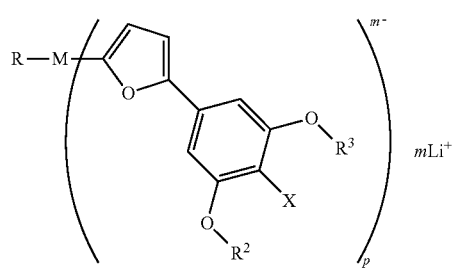

H1 wherein
- M is a Group I metal, a Group II metal, Cu, or Zn,
- R, $R^2$, and $R^3$ are each independently $C_{(1-6)}$alkyl,
- X is Cl or Br,
- m is 1, 2, 3, or 4, and
- p is 1, 2, 3, or 4;

according to the following General Scheme (II):

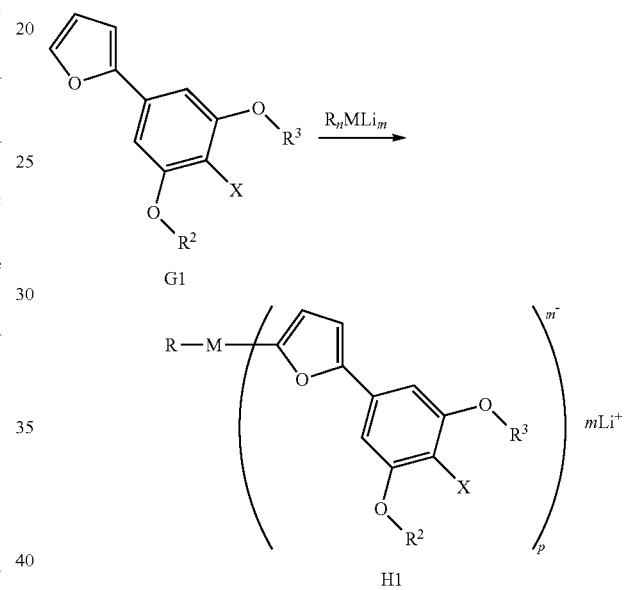

which process comprises:
- preparing in a solvent solution a lithium alkyl metal base from $R_n$—Li and a metal halide comprising M, wherein n is 1, 2, 3 4, or 5; and
- preparing a mixed metal lithiate H1 from G1 and the lithium alkyl metal base.

In one embodiment, a process is provided to prepare a compound of Formula (III):

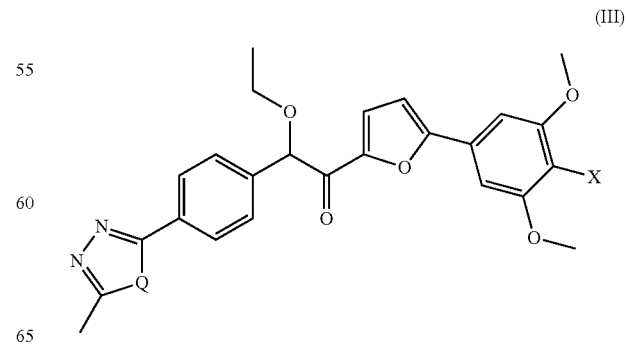

(III)

wherein Q is O or S and X is Cl or Br, according to the following General Scheme (III):

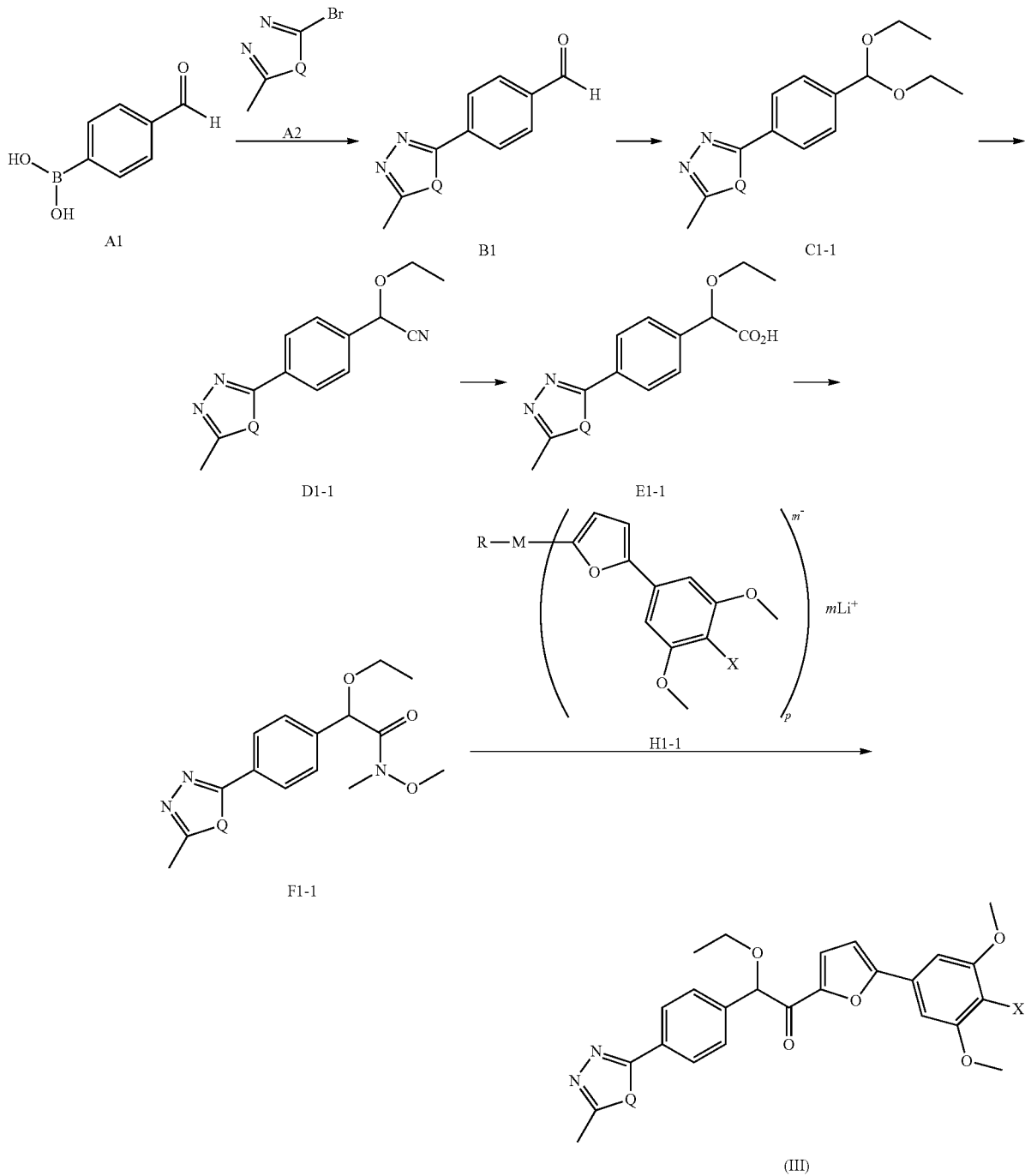

which process comprises:
  converting boronic acid A1 to carbaldehyde B1 through activation of the boronic acid with an activating reactant A2;
  converting carbaldehyde B1 to acetal C1-1 under acid catalysis with a suitable source of orthoformate;
  converting acetal C1-1 to nitrile D1-1 through catalyzed cyanation with a metal catalyst and a cyanide source;
  hydrolyzing D1-1 with a suitable acid to give carboxylic acid E1-1;
  converting carboxylic acid E1-1 to amide F1-1 with a suitable base, a suitable coupling reagent, and a source amine;
  converting amide F1-1 to a compound of Formula (III) with an anionic coupling reagent having structure H1-1,
  wherein
  M is a Group I metal, a Group II metal, Cu, or Zn;
  R is $C_{(1-6)}$alkyl;
  m is 1, 2, 3, or 4;
  p is 1, 2, 3, or 4; and optionally converting the compound of Formula (III) to a salt.

Another aspect of the invention provides a process to prepare a compound of Formula H1-1:

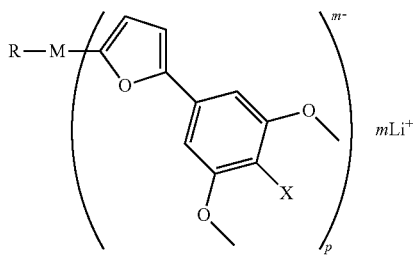

H1-1 wherein
M is a Group I metal, a Group II metal, Cu, or Zn,
R is $C_{(1-6)}$alkyl,
X is Cl or Br,
m is 1, 2, 3, or 4, and
p is 1, 2, 3, or 4;
according to the following General Scheme (IV):

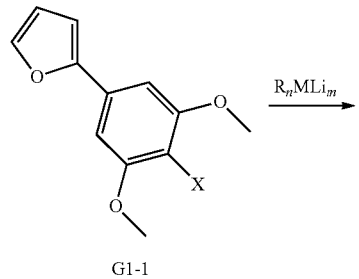

G1-1

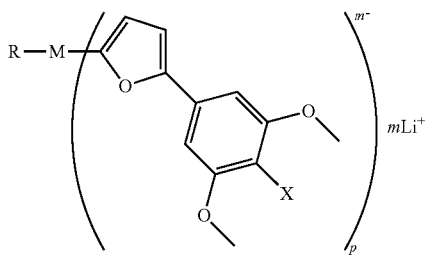

H1-1 which process comprises:
preparing in a solvent solution a lithium alkyl metal base from $R_n$—Li and a metal halide comprising M, wherein n is 1, 2, 3 4, or 5; and
preparing a mixed metal lithiate H1-1 from G1-1 and the lithium alkyl metal base.

Another aspect of the invention provides a process to prepare Compounds 1001-1003 or a salt thereof in accordance with the above General Scheme (I).

Another aspect of the invention provides a process to prepare Compounds 1001-1003 or a salt thereof in accordance with the above General Scheme (III).

Another aspect of the invention provides novel intermediates useful in the production of compounds of Formula (II), Formula (III), or Compounds 1001-1003.

In certain embodiments, the invention provides an intermediate compound having the structure of Formula H1:

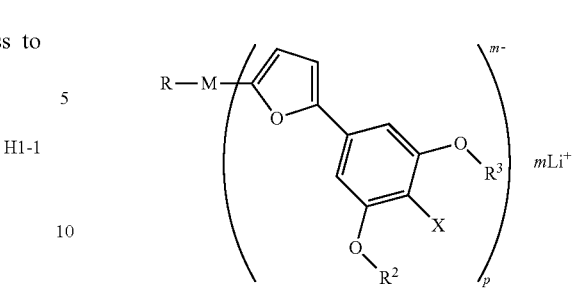

H1 wherein
M is a Group I metal, a Group II metal, Cu, or Zn,
R, $R^2$, and $R^3$ are each independently $C_{(1-6)}$alkyl,
X is Cl or Br,
m is 1, 2, 3, or 4, and
p is 1, 2, 3, or 4.

In certain embodiments, the invention provides one or more intermediates selected from:

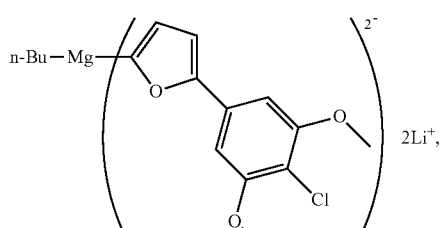

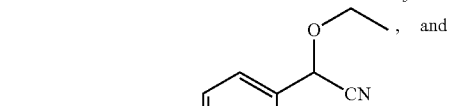, and

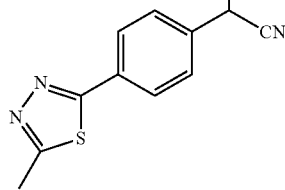

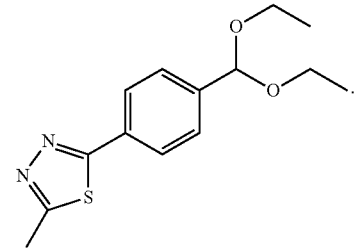.

These and other aspects of the invention will be apparent upon reference to the following detailed description. To this end, various references are set forth herein which describe in more detail certain background information, procedures, compounds and/or compositions, and are each hereby incorporated by reference in their entirety.

DETAILED DESCRIPTION

Definitions

Terms not specifically defined herein should be given the meanings that would be given to them by one of skill in the art in light of the disclosure and the context. As used throughout the present application, however, unless specified to the contrary, the following terms have the meaning indicated:

"Amino" refers to the —NH$_2$ radical.

"Cyano" refers to the —CN radical.

"Hydroxy" or "hydroxyl" refers to the —OH radical.

"Imino" refers to the =NH substituent.

"Nitro" refers to the —NO$_2$ radical.

"Oxo" refers to the =O substituent.

"Thioxo" refers to the =S substituent.

"$C_{1-6}$alkyl" means a straight chain or branched, noncyclic or cyclic, unsaturated or saturated aliphatic hydrocarbon radical containing from 1 to 6 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"$C_{1-6}$alkylene" or "$C_{1-6}$alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to six carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain.

"$C_{1-6}$alkoxy" refers to a radical of the formula —OR$_a$ where R$_a$ is an alkyl radical as defined above, for example, methoxy, ethoxy and the like.

"Aryl" means a hydrocarbon ring system radical comprising hydrogen, 6 to 18 carbon atoms and at least one aromatic ring. The aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene.

"$C_{1-6}$aralkyl" means a radical of the formula —R$_b$—R$_c$ where R$_b$ is an alkylene chain as defined above and R$_c$ is one or more aryl radicals as defined above, for example, benzyl, diphenylmethyl and the like.

"Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like.

"Halo" or "halogen" refers to bromo, chloro, fluoro or iodo.

"$C_{1-6}$haloalkyl" refers to a $C_{1-6}$alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like.

"Heterocycle" or "heterocyclyl" means a 4- to 7-membered monocyclic, or 7- to 10-membered bicyclic, heterocyclic ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. An aromatic heterocycle is referred to herein as a "heteroaryl", and includes (but is not limited to) furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, oxadiazolyl, thiadiazolyl, benzisoxazolyl, triazolyl, tetrazolyl, indazolyl and quinazolinyl. In addition to the heteroaryls listed above, heterocycles also include morpholinyl, pyrrolidinonyl, pyrrolidinyl, piperidinyl, piperazinyl, and the like. In addition, heterocycles also include benzothiophen-2-yl, 2,3-dihydrobenzo-1,4-dioxin-6-yl, benzo-1,3-dioxol-5-yl and the like.

The term "substituted" as used herein (for example, in the context of a substituted heterocyclyl or substituted aryl) means that at least one hydrogen atom is replaced with a substituent. "Substituents" within the context of this invention include halogen, hydroxy, oxo, cyano, nitro, imino, thioxo, amino, alkylamino, dialkylamino, alkyl, alkoxy, alkylthio, haloalkyl, aryl, aralkyl, heteroaryl, heteroarylalkyl, heterocycle and heterocyclealkyl, as well as —NR$_a$R$_b$, —NR$_a$C(=O)R$_b$, —NR$_a$C(=O)NR$_a$NR$_b$, —NR$_a$C(=O)OR$_b$—NR$_a$SO$_2$R$_b$, —C(=O)R$_a$, —C(=O)OR$_a$, —C(=O)NR$_a$R$_b$, —OC(=O)NR$_a$R$_b$, —OR$_a$, —SR$_a$, —SOR$_a$, —S(=O)$_2$R$_a$, —OS(=O)$_2$R$_a$, —S(=O)$_2$OR$_a$, =NSO$_2$R$_a$ and —SO$_2$NR$_a$R$_b$. In the foregoing, R$_a$ and R$_b$ in this context may be the same or different and independently hydrogen, alkyl, haloalkyl, cycloalkyl, aryl, aralkyl, heterocyclyl. In addition, the foregoing substituents may be further substituted with one or more of the above substituents.

The compounds of the present invention may generally be utilized as the free acid or free base. Alternatively, the compounds of this invention may be used in the form of acid or base addition salts. Acid addition salts of the free amino compounds of the present invention may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" of formulas (I), (II), and (III) is intended to encompass any and all acceptable salt forms.

Embodiments of the Invention

As mentioned above, the present invention is directed to a synthetic process for preparing compounds of Formula (II) and Formula (III), in particular, Compounds 1001-1003, using the synthetic steps described herein. The present invention is also directed to particular individual steps of this process and particular individual intermediates used in this process.

In the synthetic schemes below, unless specified otherwise, all the substituent groups in the chemical formulas shall have the meanings as in Formula (II). The reactants used in the examples below may be obtained either as described herein, or if not described herein, are themselves either commercially available or may be prepared from commercially available materials by methods known in the art. Certain starting materials, for example, may be obtained by methods described in International PCT Application Publication No. WO 2011/112828.

Optimum reaction conditions and reaction times may vary depending upon the particular reactants used. Unless otherwise specified, solvents, temperatures, pressures, and other reaction conditions may be readily selected by one of ordinary skill in the art. Typically, reaction progress may be monitored by High Pressure Liquid Chromatography (HPLC) or Nuclear Magnetic Resonance (NMR) spectroscopy, if desired, and intermediates and products may be purified by chromatography and/or by recrystallization or precipitation with or without treatment with carbon.

In one embodiment, the present invention is directed to the multi-step synthetic method for preparing compounds of Formula (II), and, in particular, Compounds 1001-1003, as set forth in General Schemes (I) and (II). In one embodiment, a process is provided to prepare a compound of Formula (II):

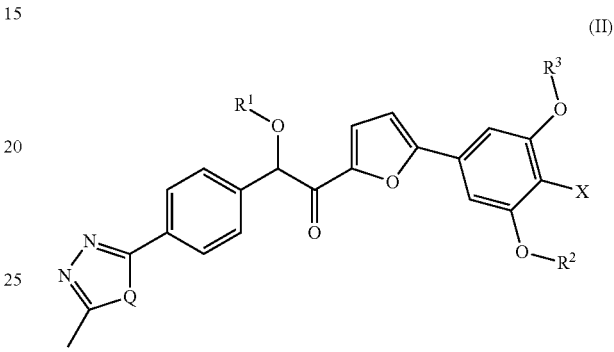

(II)

wherein
Q is S or O,
X is Cl or Br, and
$R^1$, $R^2$, and $R^3$ are each independently $C_{(1-6)}$alkyl,
according to the following General Scheme (I):

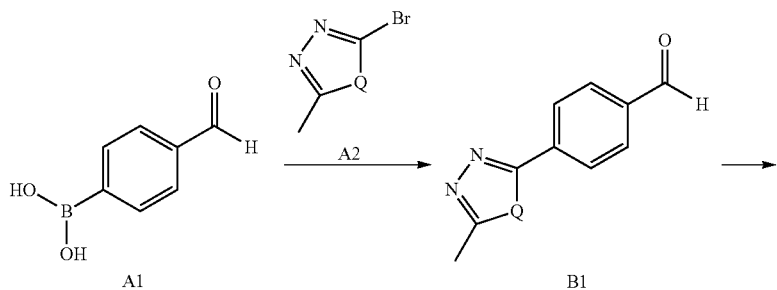

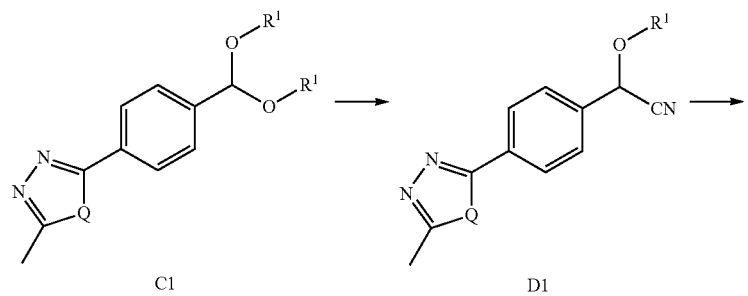

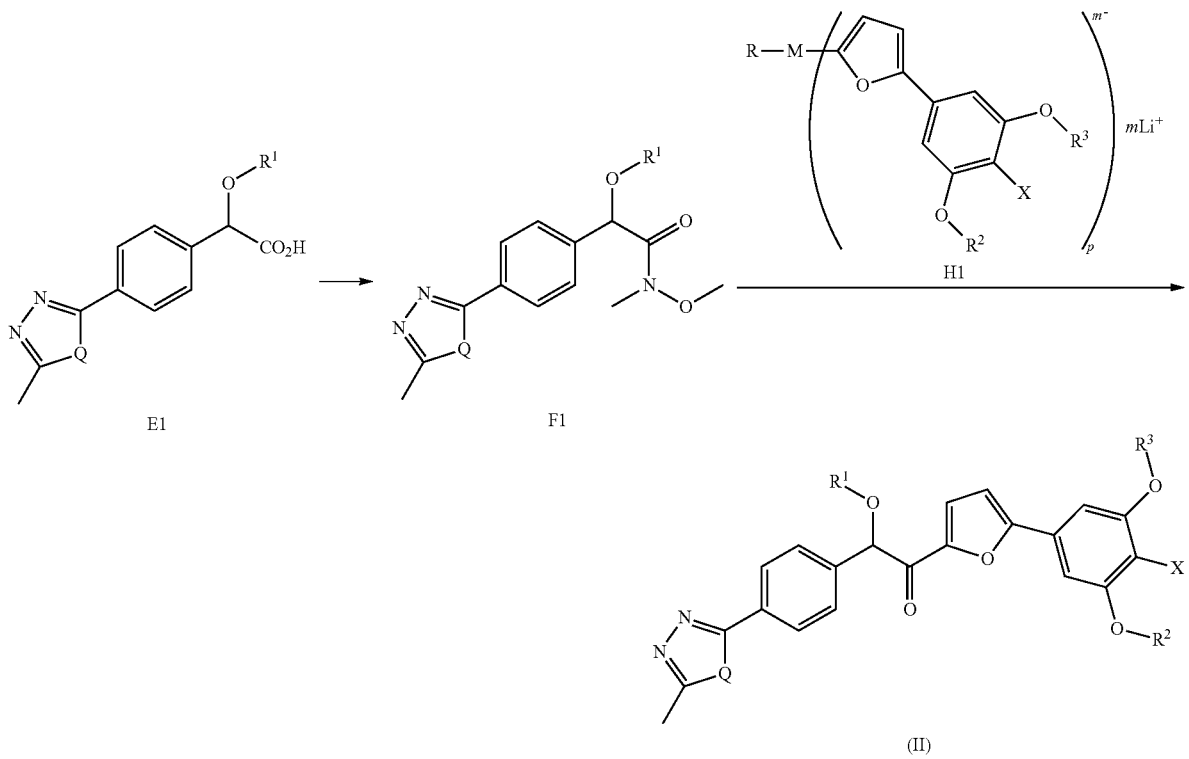

which process comprises:
- converting boronic acid A1 to carbaldehyde B1 through activation of the boronic acid with an activating reactant A2;
- converting carbaldehyde B1 to acetal C1 under acid catalysis with a suitable source of orthoformate;
- converting acetal C1 to nitrile D1 through catalyzed cyanation with a metal catalyst and a cyanide source;
- hydrolyzing D1 with a suitable acid to give carboxylic acid E1;
- converting carboxylic acid E1 to amide F1 with a suitable base, a suitable coupling reagent, and a source amine;
- converting amide F1 to a compound of Formula (II) with an anionic coupling reagent having structure H1, wherein
M is a Group I metal, a Group II metal, Cu, or Zn;
R, $R^2$, and $R^3$ are each independently $C_{(1-6)}$alkyl;
m is 1, 2, 3, or 4;
p is 1, 2, 3, or 4; and
optionally converting the compound of Formula (II) to a salt.

In further embodiments of the process of General Scheme (I), Q is O.

In further embodiments of the process of General Scheme (I), Q is S.

In further embodiments of the process of General Scheme (I), X is Cl.

In further embodiments of the process of General Scheme (I), X is Br.

In further embodiments of the process of General Scheme (I), M is a Group II metal.

In further embodiments of the process of General Scheme (I), M is Mg.

In further embodiments of the process of General Scheme (I), $R^1$ is methyl, ethyl or propyl.

In further embodiments of the process of General Scheme (I), $R^1$ is ethyl.

In further embodiments of the process of General Scheme (I), $R^2$ is methyl, ethyl or propyl.

In further embodiments of the process of General Scheme (I), $R^2$ is methyl.

In further embodiments of the process of General Scheme (I), $R^3$ is methyl, ethyl or propyl.

In further embodiments of the process of General Scheme (I), $R^3$ is methyl.

In further embodiments of the process of General Scheme (I), R is butyl. In further embodiments of the process of General Scheme (I), the acid catalyst used to create acetal C1 is para-toluenesulfonic acid monohydrate.

In further embodiments of the process of General Scheme (I), the suitable source of orthoformate is triethyl orthoformate.

In further embodiments of the process of General Scheme (I), the metal catalyst of the cyanation step is a cobalt salt.

In further embodiments of the process of General Scheme (I), the metal catalyst of the cyanation step is $CoCl_2$.

In further embodiments of the process of General Scheme (I), the cyanide source is trimethylsilyl cyanide.

In further embodiments of the process of General Scheme (I), the suitable acid of the hydrolysis step is HCl.

In further embodiments of the process of General Scheme (I), the suitable base of the amidation step is triethylamine.

In further embodiments of the process of General Scheme (I), the suitable coupling reagent of the amidation step is propylphosphonic anhydride.

In further embodiments of the process of General Scheme (I), the source amine is N,O-dimethylhydroxylamine hydrochloride.

In further embodiments of the process of General Scheme (I), the compound of Formula (II) is:

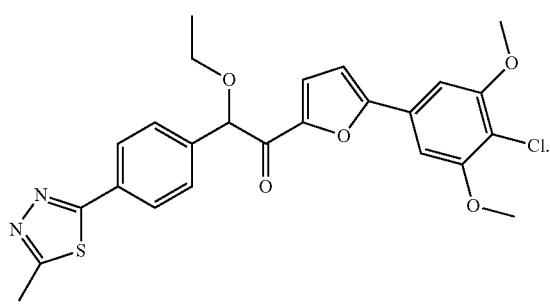

In further embodiments of the process of General Scheme (I), the compound of Formula (II) is:

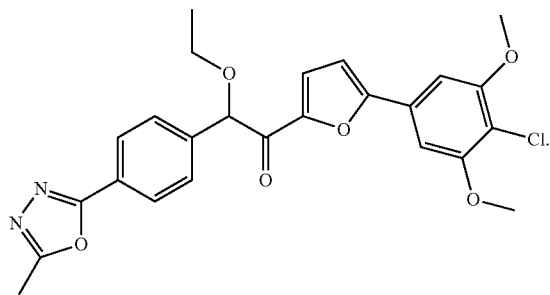

In further embodiments of the process of General Scheme (I), the compound of Formula (II) is:

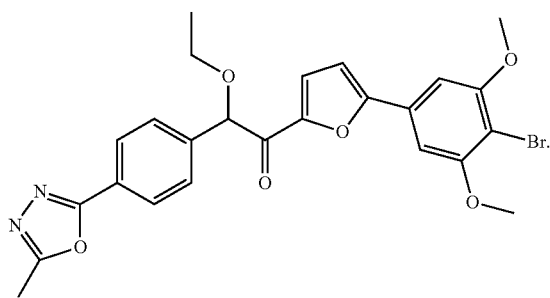

In another embodiment, a process is provided to prepare a compound of Formula H1:

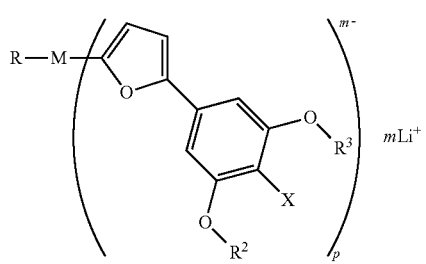

wherein
M is a Group I metal, a Group II metal, Cu, or Zn,
R, $R^2$, and $R^3$ are each independently $C_{(1-6)}$alkyl,
X is Cl or Br,
m is 1, 2, 3, or 4, and
p is 1, 2, 3, or 4;
according to the following General Scheme (II):

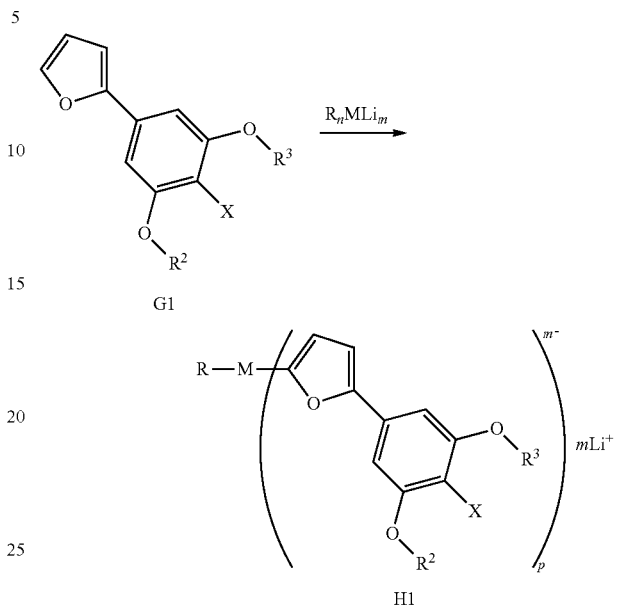

which process comprises:
preparing in a solvent solution a lithium alkyl metal base from $R_n$—Li and a metal halide comprising M, wherein n is 1, 2, 3 4, or 5; and
preparing a mixed metal lithiate H1 from G1 and the lithium alkyl metal base.

In further embodiments of the process of General Scheme (II), $R^2$ is methyl, ethyl, or propyl.

In further embodiments of the process of General Scheme (II), $R^2$ is methyl.

In further embodiments of the process of General Scheme (II), $R^3$ is methyl, ethyl, or propyl.

In further embodiments of the process of General Scheme (II), $R^3$ is methyl.

In further embodiments of the process of General Scheme (II), R is butyl.

In further embodiments of the process of General Scheme (II), X is Cl.

In further embodiments of the process of General Scheme (II), X is Br.

In further embodiments of the process of General Scheme (II), M is a Group (I) metal.

In further embodiments of the process of General Scheme (II), M is a Group II metal.

In further embodiments of the process of General Scheme (II), M is Mg.

In further embodiments of the process of General Scheme (II), M is Cu.

In further embodiments of the process of General Scheme (II), M is Zn.

In further embodiments of the process of General Scheme (II), the lithium alkyl metal base is a lithium alkylmagnesate base.

In further embodiments of the process of General Scheme (II), the lithium alkyl metal base is $Bu_4MgLi_2$.

In further embodiments of the process of General Scheme (II), the compound of Formula H1 is a compound of Formula H1-1:

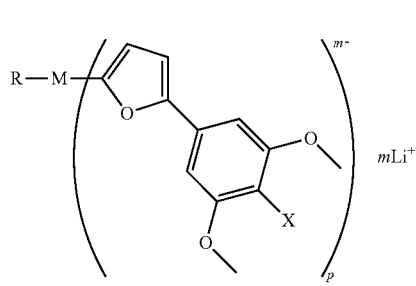

H1-1

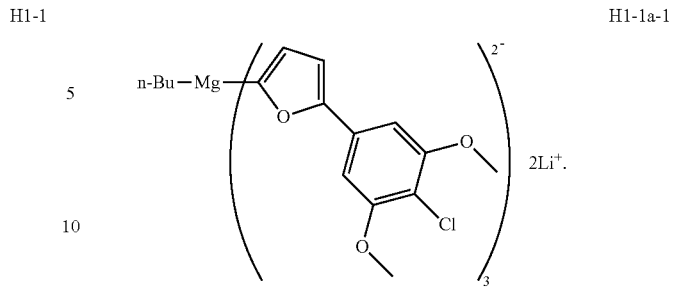

H1-1a-1 wherein
  M is a Group I metal, a Group II metal, Cu, or Zn,
  R is $C_{(1-6)}$alkyl,
  X is Cl or Br,
  m is 1, 2, 3, or 4, and
  p is 1, 2, 3, or 4.

In further embodiments of the process of General Scheme (II), the compound of Formula H1-1 is:

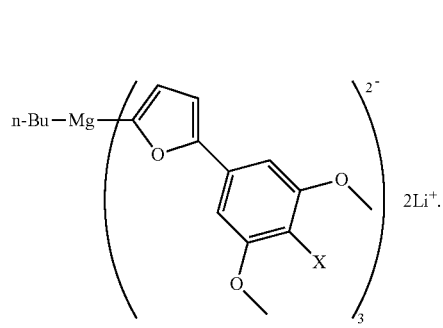

H1-1a

In further embodiments of the process of General Scheme (II), the compound of Formula H1-1a is:

In one embodiment, the present invention is directed to the multi-step synthetic method for preparing compounds of Formula (II) and, in particular, Compounds 1001-1003, as set forth in General Schemes (III) and (IV). In one embodiment, a process is provided to prepare a compound of Formula (III):

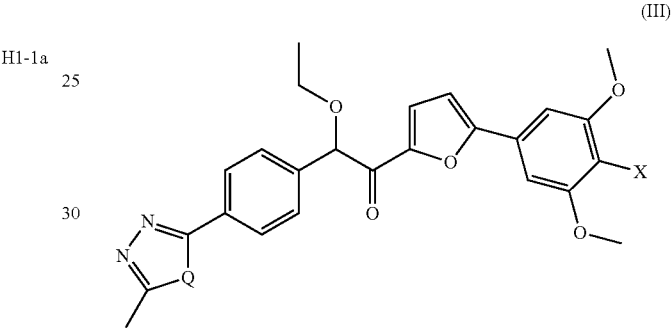

(III)

wherein Q is S or O and X is Cl or Br,
according to the following General Scheme (III):

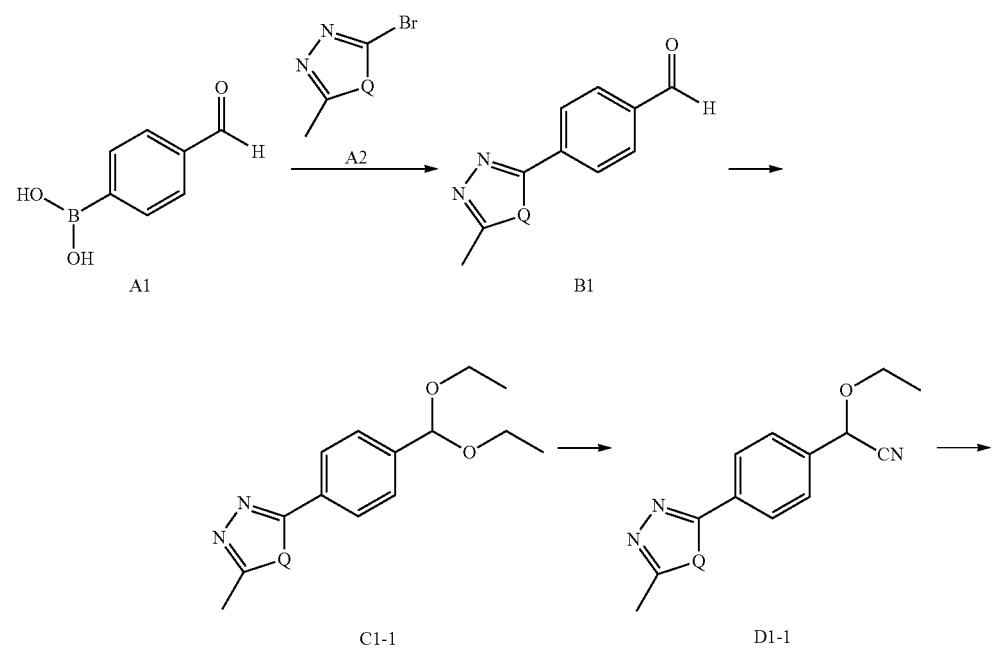

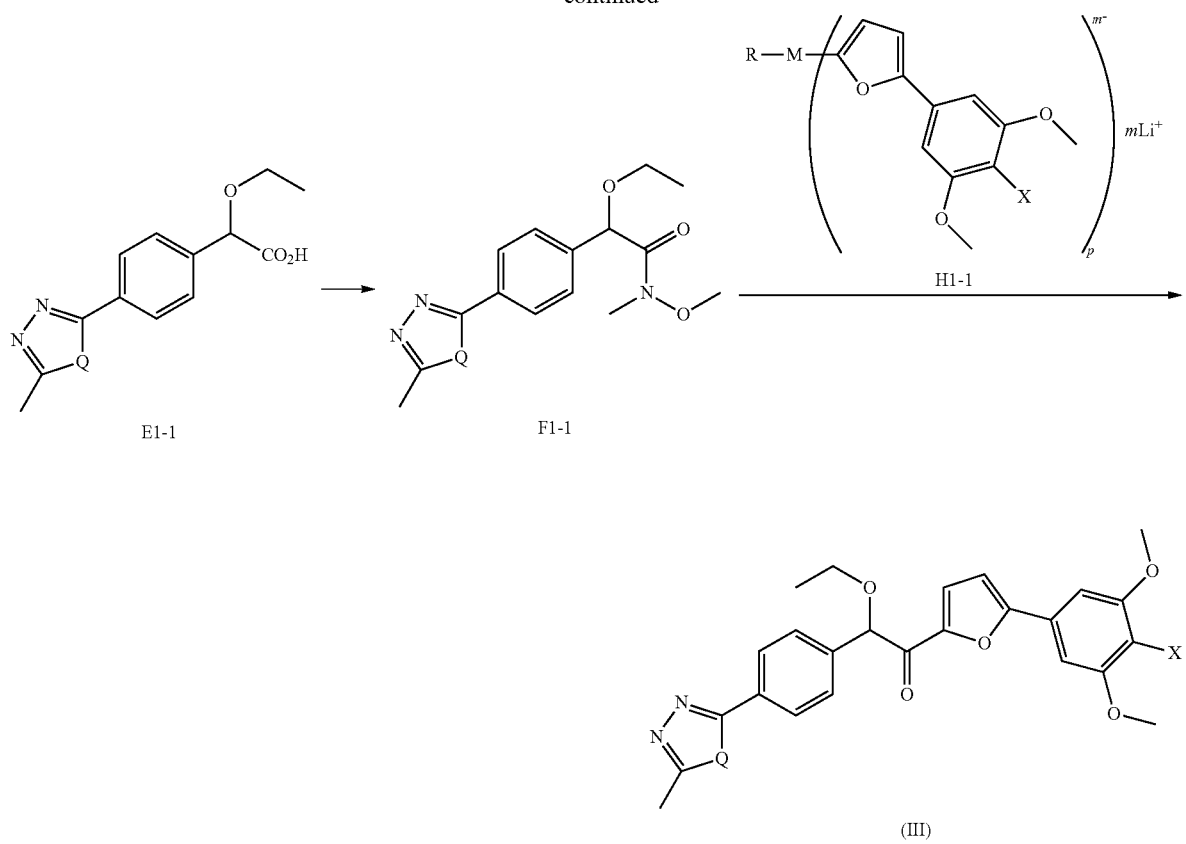

which process comprises:
- converting boronic acid A1 to carbaldehyde B1 through activation of the boronic acid with an activating reactant A2;
- converting carbaldehyde B1 to acetal C1-1 under acid catalysis with a suitable source of orthoformate;
- converting acetal C1-1 to nitrile D1-1 through catalyzed cyanation with a metal catalyst and a cyanide source;
- hydrolyzing D1-1 with a suitable acid to give carboxylic acid E1-1;
- converting carboxylic acid E1-1 to amide F1-1 with a suitable base, a suitable coupling reagent, and a source amine;
- converting amide F1-1 to a compound of Formula (III) with an anionic coupling reagent having structure H1-1,
  wherein
  M is a Group I metal, a Group II metal, Cu, or Zn;
  R is $C_{(1-6)}$alkyl;
  m is 1, 2, 3, or 4;
  p is 1, 2, 3, or 4; and
- optionally converting the compound of Formula (III) to a salt.

In further embodiments of the process of General Scheme (III), Q is O.

In further embodiments of the process of General Scheme (III), Q is S.

In further embodiments of the process of General Scheme (III), X is Cl.

In further embodiments of the process of General Scheme (III), X is Br.

In further embodiments of the process of General Scheme (III), M is a Group II metal.

In further embodiments of the process of General Scheme (III), M is Mg.

In further embodiments of the process of General Scheme (III), R is butyl.

In further embodiments of the process of General Scheme (III), the acid catalyst used to create acetal C1-1 is para-toluenesulfonic acid monohydrate.

In further embodiments of the process of General Scheme (III), the suitable source of orthoformate is triethyl orthoformate.

In further embodiments of the process of General Scheme (III), the metal catalyst of the cyanation step is a cobalt salt.

In further embodiments of the process of General Scheme (III), the metal catalyst of the cyanation step is $CoCl_2$.

In further embodiments of the process of General Scheme (III), the cyanide source is trimethylsilyl cyanide.

In further embodiments of the process of General Scheme (III), the suitable acid of the hydrolysis step is HCl.

In further embodiments of the process of General Scheme (III), the suitable base of the amidation step is triethylamine.

In further embodiments of the process of General Scheme (III), the suitable coupling reagent of the amidation step is propylphosphonic anhydride.

In further embodiments of the process of General Scheme (III), the source amine is N,O-dimethylhydroxylamine hydrochloride.

In further embodiments of the process of General Scheme (III), the compound of Formula (III) is:

In further embodiments of the process of General Scheme (III), the compound of Formula (III) is:

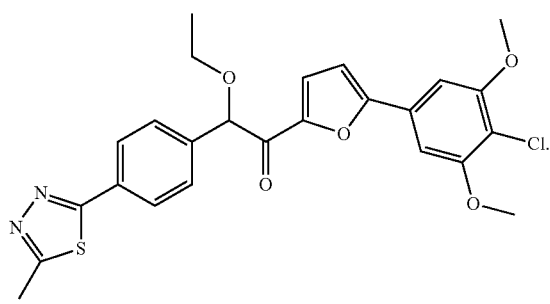

In further embodiments of the process of General Scheme (III), the compound of Formula (III) is:

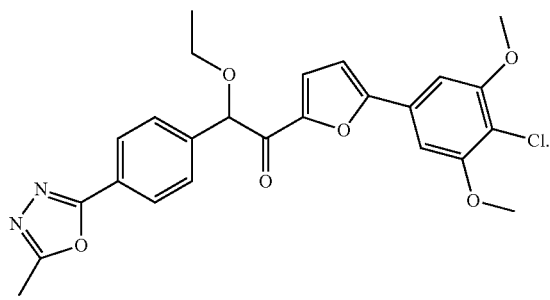 [SMILES: CCOC(C(=O)c1ccc(-c2cc(OC)c(Br)c(OC)c2)o1)c1ccc(-c2nnc(C)o2)cc1]

In further embodiments of the process of General Scheme (III), the compound of Formula (III) is:

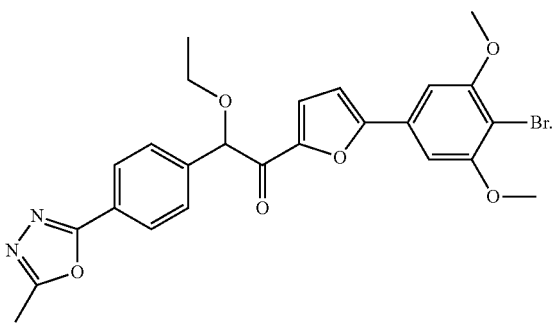 [SMILES: CCOC(C(=O)c1ccc(-c2cc(OC)c(Br)c(OC)c2)o1)c1ccc(-c2nnc(C)o2)cc1]

In another embodiment, a process is provided to prepare a compound of Formula H1-1:

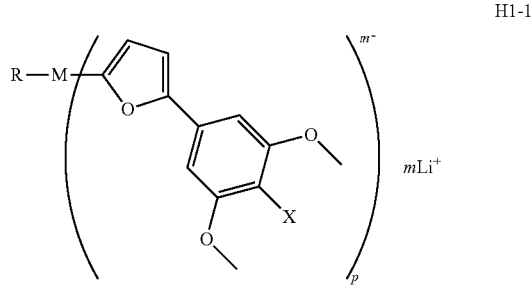

H1-1 wherein
M is a Group I metal, a Group II metal, Cu, or Zn,
R is $C_{(1-6)}$alkyl,
X is Cl or Br,
m is 1, 2, 3, or 4, and
p is 1, 2, 3, or 4;
according to the following General Scheme (IV):

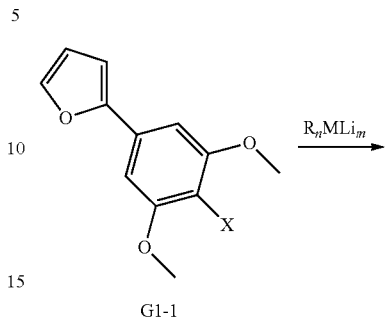

which process comprises:
preparing in a solvent solution a lithium alkyl metal base from $R_n$—Li and a metal halide comprising M, wherein n is 1, 2, 3 4, or 5; and
preparing a mixed metal lithiate H1-1 from G1-1 and the lithium alkyl metal base.

In further embodiments of the process of General Scheme (IV), X is Cl.

In further embodiments of the process of General Scheme (IV), X is Br.

In further embodiments of the process of General Scheme (IV), M is a Group (I) metal.

In further embodiments of the process of General Scheme (IV), M is a Group II metal.

In further embodiments of the process of General Scheme (IV), M is Mg.

In further embodiments of the process of General Scheme (IV), M is Cu.

In further embodiments of the process of General Scheme (IV), M is Zn.

In further embodiments of the process of General Scheme (IV), R is butyl.

In further embodiments of the process of General Scheme (IV), the lithium alkyl metal base is a lithium alkylmagnesate base.

In further embodiments of the process of General Scheme (IV), the lithium alkyl metal base is $Bu_4MgLi_2$.

In further embodiments of the process of General Scheme (IV), the compound of Formula H1-1 is a compound of Formula H1-1a:

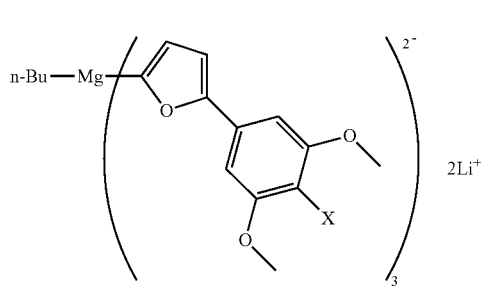

In further embodiments of the process of General Scheme (II), the compound of Formula H1-1a is:

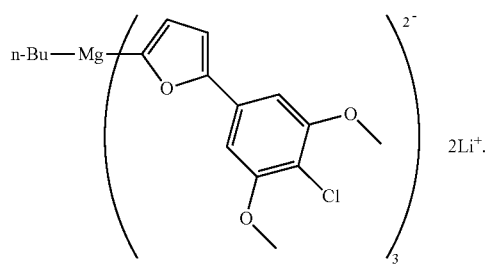

Additional embodiments of the invention are directed to the individual steps of the multistep general synthetic methods described above in (I)-(IV) and the individual intermediates used in these steps. These intermediates of the present invention are described in detail below. All substituent groups in the intermediates described below are as defined in the multi-step method above.

Preferred anionic coupling reagents are selected from a compound having a structure according to Formula H1:

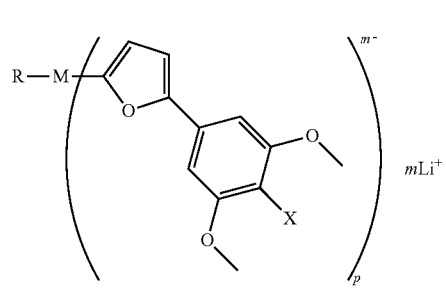

wherein
 M is a Group I metal, a Group II metal, Cu, or Zn,
 R, R², and R³ are each independently C$_{(1-6)}$alkyl,
 X is Cl or Br,
 m is 1, 2, 3, or 4, and
 p is 1, 2, 3, or 4.

Preferred anionic coupling reagents are selected from a compound having a structure according to Formula H1-1:

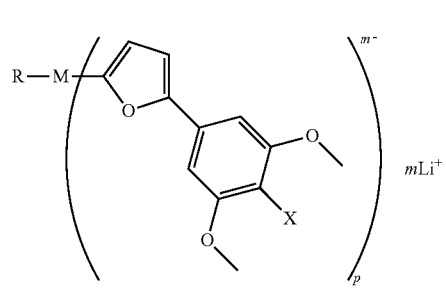

wherein
 M is a Group I metal, a Group II metal, Cu, or Zn,
 R is C$_{(1-6)}$alkyl,
 X is Cl or Br,
 m is 1, 2, 3, or 4, and
 p is 1, 2, 3, or 4.

In another embodiment, M is Mg.

Preferred anionic coupling reagents are selected from a compound having a structure according to Formula H1-1a:

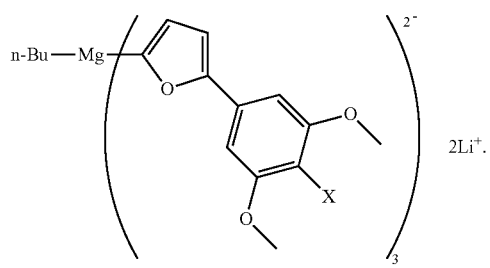

wherein X is Cl or Br.

In another embodiment, X is Cl.

In another embodiment, X is Br.

In another embodiment, the anionic coupling reagent has the following structure:

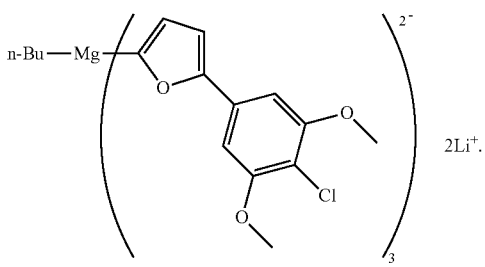

In another embodiment, a preferred nitrile intermediate has the following structure:

In still another embodiment, a preferred acetal intermediate has the following structure:

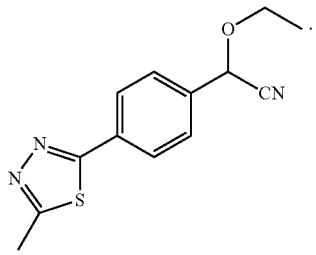

D1-1

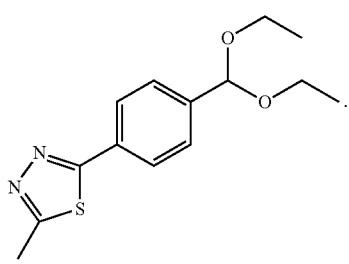

C1-1

EXAMPLES

In order that this invention may be more fully understood, the following examples are set forth. These examples are for the purpose of illustrating embodiments of this invention, and are not to be construed as limiting the scope of the invention in any way. The reactants used in the examples below may be obtained either as described herein, or if not described herein, are themselves either commercially available or may be prepared from commercially available materials by methods known in the art.

Unless otherwise specified, solvents, temperatures, pressures, and other reaction conditions may be readily selected by one of ordinary skill in the art. Typically, reaction progress may be monitored by High Pressure Liquid Chromatography (HPLC), if desired, and intermediates and products may be purified by chromatography and/or by recrystallization or precipitation with or without treatment with carbon.

In one embodiment, the present invention is directed to the multi-step synthetic method for preparing Compound 1001 as set forth in Examples 1-8.

Example 1

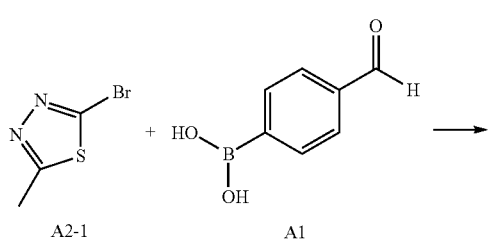

A2-1        A1

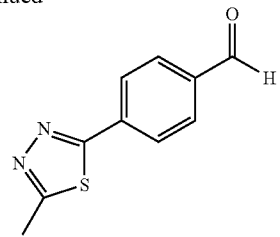

B1-1

A mixture of 2-bromo-5-methyl-1,3,4-thiadiazole A2-1 (13.1 g, 73.3 mmol), (4-formylphenyl)boronic acid A1 (10.0 g, 66.7 mmol), 2M $K_3PO_4$ (66.7 mL, 133.4 mmol) in toluene (150 mL) and ethanol (38 mL) was heated to 55° C. under nitrogen then degassed by alternately putting under vacuum and nitrogen three times for several minutes each. Tetrakis (triphenylphosphine)palladium (1.54 g, 1.33 mmol) was added, and then the mixture was degassed again. After heating for 18 hours at 80° C. and cooling to room temperature, the aqueous layer was separated. The mixture was washed with brine and the remaining organic layer was reduced in volume by distillation. Addition of heptane provided a solid which was collected by filtration to give 4-(5-methyl-1,3,4-thiadiazol-2-yl)benzaldehyde B1-1 as a solid in 85% yield.

Example 2

B1-1 (1.05 g, 5.14 mmol), EtOH (10 mL), $CH(OEt)_3$ (1.1 equiv), and para-toluenesulfonic acid monohydrate (5 mol %) were heated at 67° C. for 30 minutes. The solution was cooled, and saturated aqueous $NaHCO_3$ (10 mL) was added. The mixture was transferred to a separatory funnel with dichloromethane (20 mL). Additional water dissolved the solids and the layers were separated. The organic layer was concentrated under reduced pressure to give a mixture of solids and oil. The mixture was redissolved in dichloromethane (10 mL) and the solution was washed with water (5 mL). Solvent removal gave C1-1a (1.29 g, 90% yield).

Example 3

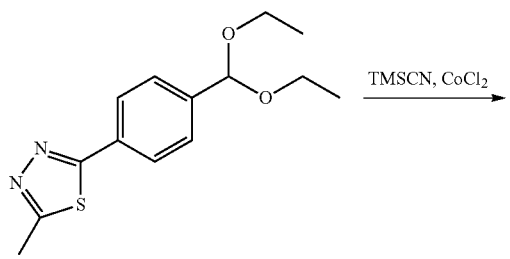

C1-1a (145 mg, 0.522 mmol) was stirred with TMSCN (100 µL, 1.5 equiv) and dichloroethane (1 mL) while CoCl$_2$ (5 mg) was added. The reaction was heated at 60° C. for 3.25 hours. Saturated aqueous NaHCO$_3$ (2 mL) and dichloromethane (5 mL) were added. The layers were separated and the organic layer was concentrated under reduced pressure to give D1-1a as an off-white solid (104 mg, 77% yield).

Example 4

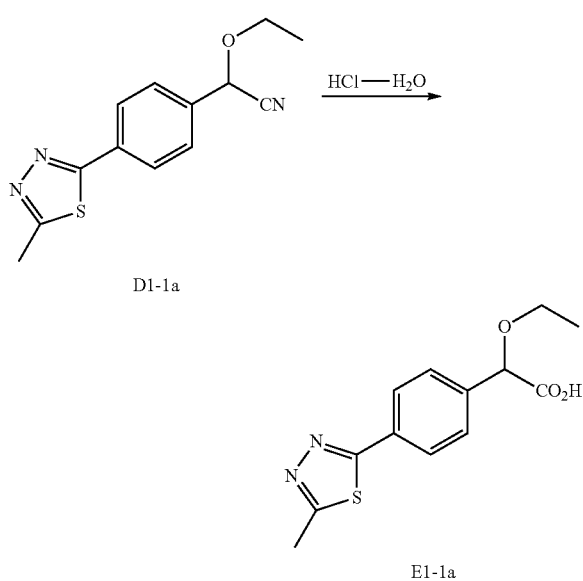

A mixture of D1-1a (1.01 g, 3.90 mmol), 1,2-dichloroethane (5.0 mL), concentrated HCl (2.0 mL) and water (1.0 mL) was heated to 70° C. for 15 hours. After cooling to room temperature, water (1 mL) was added. The organic phase was separated and additional water (5 mL) was added to the aqueous layer then extracted with dichloromethane (2×10 mL). The first organic phase was combined with the dichloromethane extracts and the mixture was concentrated under reduced pressure to provide E1-1a as a tan solid (1.02 g, 94% yield).

Example 5

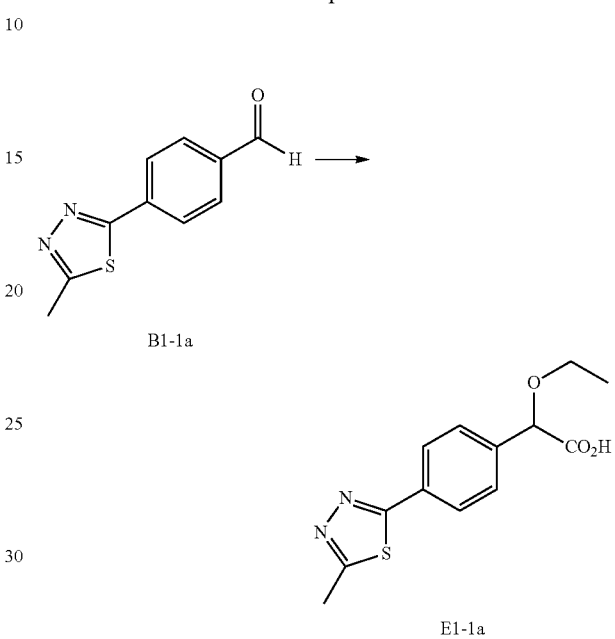

Alternatively, steps to form E1-1a from B1-1a can be performed without isolation of purified synthetic intermediates.

To a reactor was charged B1-1a (100.4 g, 0.490 mol) with para-toluenesulfonic acid (catalytic amount) and toluene at room temperature. Ethanol and triethyl orthoformate were charged, followed by a toluene rinse each. The batch was heated to 45° C. More para-toluenesulfonic acid (catalytic amount) was added and heating was continued for 2 hours Anhydrous K$_2$CO$_3$ was added and the batch was partially concentrated under vacuum. Toluene was added, and the batch was again partially concentrated. The batch was filtered to remove solids. The reactor and filter were rinsed with toluene.

To this solution was charged CoCl$_2$ (catalytic amount) and TMSCN at 20° C. The batch was heated at 75° C. overnight. To the obtained mixture, methyl tert-butyl ether was slowly charged at 70-80° C. The batch was cooled to room temperature then filtered and the cake was rinsed with methyl tert-butyl ether and water. The wet cake was dried briefly to yield 154.6 g D1-1a as a wet cake.

The wet cake of D1-1a was charged to a reactor followed by concentrated HCl and water at 20-25° C. The batch was heated to 60° C. for 3.5 hours. Celite and acetonitrile were added and the batch was filtered over Darco G60 carbon and Celite. The filtrate was charged to the reactor and heated to 60-70° C. Water was slowly added and then cooled down to 25° C. The solid was collected by filtration, washed with water and dried to give 105 g E1-1a (77% yield) as a white solid.

Example 6

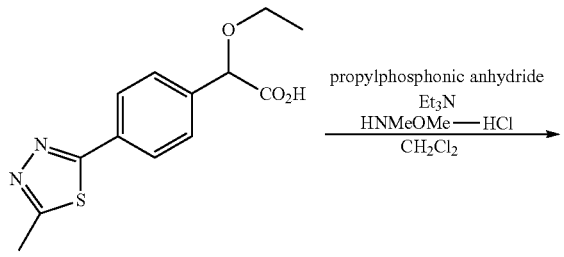

E1-1a propylphosphonic anhydride
Et₃N
HNMeOMe—HCl
$\xrightarrow{CH_2Cl_2}$

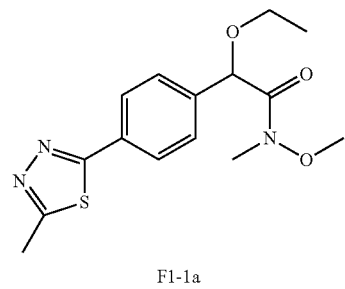

F1-1a

To a reactor was charged E1-1a (117.2 g, 0.392 mol as hydrate, 6.3% water) with N,O-dimethylhydroxylamine hydrochloride (61.5 g, 1.5 equiv) and dichloromethane (936 mL). The mixture was stirred to form a slurry. Triethylamine (272 mL) was charged slowly over 15 minutes, resulting in a slight exotherm. Propylphosphonic anhydride (376 g as 50 wt % solution in dichloromethane, 1.5 equiv) was charged slowly over 1 hour. Water (470 mL) was charged over 10 minutes. The layers were separated and the aqueous phase was extracted with dichloromethane. The organic phases were combined and washed with saturated sodium bicarbonate solution, and 1N HCl solution. The batch was concentrated somewhat under reduced pressure. Isopropyl acetate was added, and the mixture was slightly concentrated again under reduced pressure. This was repeated twice. The mixture was heated, seeded at 50° C., heptane was added then it was cooled to room temperature. The solid was collected by filtration and washed with a mixture of isopropylacetate-heptane. F1-1a was obtained in 88% yield and purity of 99%.

Example 7

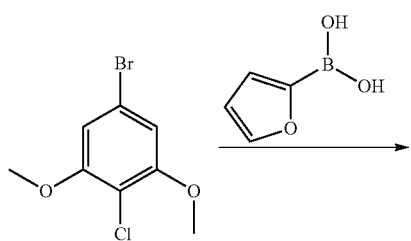

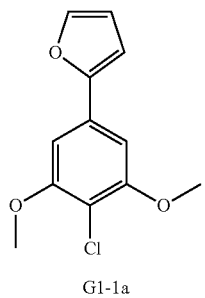

G1-1a 2-(4-Chloro-3,5-dimethoxyphenyl)furan G1-1a was synthesized according to the procedure reported in International PCT Application Publication No. WO 2008/040669 as follows. To a flask containing 3,5-dimethoxy-4-chloro-bromobenzene (5 g, 20 mmol), 2-furylboronic acid (2.45 g, 21.9 mmol), and 2M Na₂CO₃ (25 mL) was added tetrahydrofuran (50 mL). The mixture was degassed by alternately putting under house vacuum and nitrogen three times for several minutes each. Tetrakis(triphenylphosphine)palladium (0.46 g, 0.4 mmol) was added and the mixture was degassed again then heated at 60° C. for 17 hrs. Volatiles were removed in vacuo then methanol (10 mL) was added and the slurry was stirred at 60° C. for 2 h. The mixture was cooled to room temperature, and the solids were collected. The solid was slurried in hot methanol then filtered and dried to give 2-(4-chloro-3,5-dimethoxyphenyl) furan (3.18 g, 67% yield).

Example 8

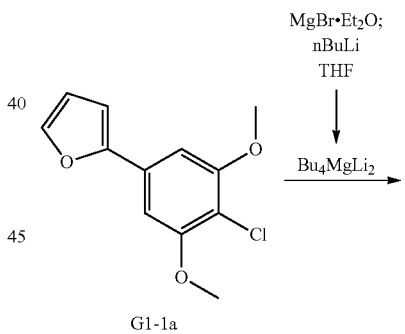

G1-1a

MgBr·Et₂O;
nBuLi
THF
$\downarrow$

Bu₄MgLi₂

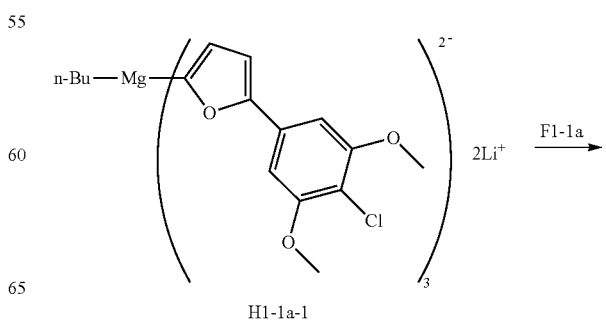

H1-1a-1

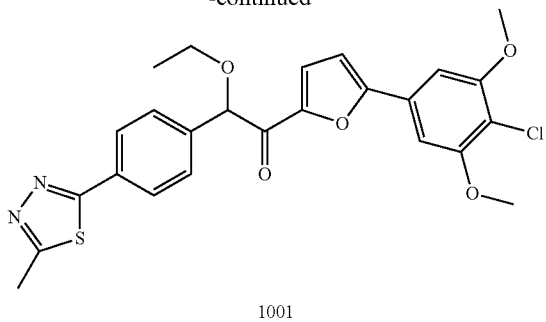

1001

All solvents were degassed by sparging with $N_2$ for a minimum of 20 minutes. $MgBr_2 \cdot Et_2O$ (3.91 g, 15.2 mmol) was added to tetrahydrofuran (39.0 mL) in a clean dry flask (small exotherm) to give a slurry after cooling to room temperature. The mixture was cooled to −10° C. and a solution of n-BuLi (16.81 g, 2.62 M solution in hexanes) was added via syringe over 34 minutes. After stirring for 1 hour at −10° C., a solution of G1-1a (11.61 g, 48.6 mmol) in tetrahydrofuran (34.8 mL) was added over 60 minutes at a constant rate. The solution was warmed to room temperature and stored under $N_2$ overnight.

To a separate flask was added a solution of F1-1a (12.48 g, 38.9 mmol) in toluene (100.0 mL) and tetrahydrofuran (25.0 mL). The solution was cooled to −23° C. and the anion solution (prepared above) was added over 2 hours. A solution of acetic acid (7.2 mL) in water (67 mL) was added over 11 minutes, during which time the temperature increased to −10° C. The reaction was warmed to 50° C. and the aqueous phase was removed. Water (67 mL) was added and the organic phase was collected and concentrated under reduced pressure. Chromatography on silica gel (70% isopropyl acetate-heptane) gave 12.8 g of Compound 1001 (66% yield).

Example 9

Synthesis of Further Representative Compounds

The following representative compounds in Table 1 are synthesized according to (i) the foregoing procedures by selecting appropriate starting materials and (ii) known organic synthesis techniques.

TABLE 1

| Compound No. | Structure | MS m/z [M + H]+ |
|---|---|---|
| 1002 | 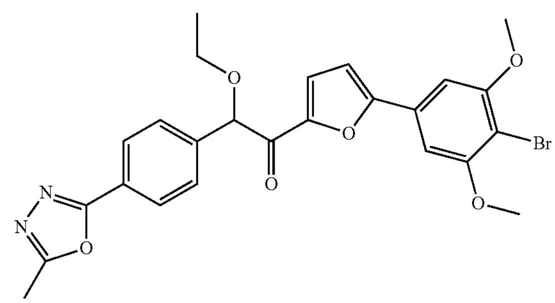 | 527.3 |
| 1003 | 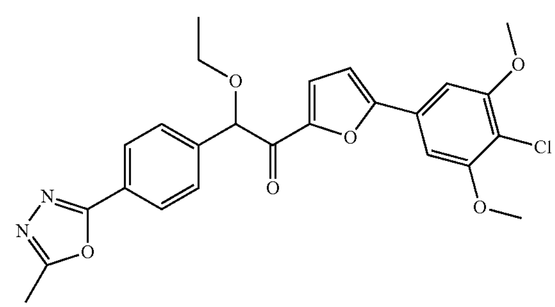 [SMILES: CCOC(C(=O)c1ccc(-c2cc(OC)c(Cl)c(OC)c2)o1)c1ccc(-c2nnc(C)o2)cc1] | 483.1 |

It will be appreciated that, although specific embodiments of the invention have been described herein for purposes of illustration, various modifications may be made without departing from the spirit and scope of the invention. Accordingly, the invention is not limited except as by the appended claims.

All of the U.S. patents, U.S. patent application publications, U.S. patent applications, foreign patents, foreign patent applications and non-patent publications referred to in this specification are incorporated herein by reference, in their entirety to the extent not inconsistent with the present description.

What is claimed is:

1. A process to prepare a compound of Formula (II):

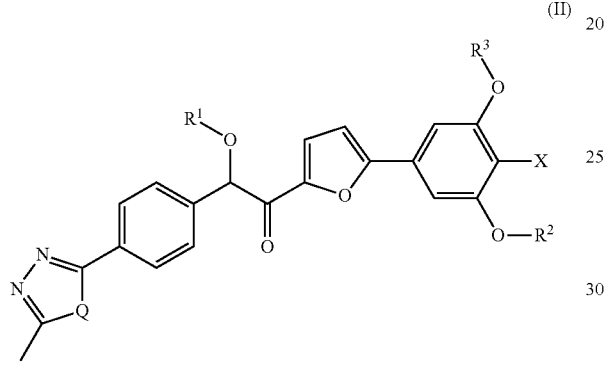

wherein

Q is S or O,

X is Cl or Br, and $R^1$, $R^2$, and $R^3$ are each independently $C_{(1-6)}$alkyl, according to the following General Scheme (I):

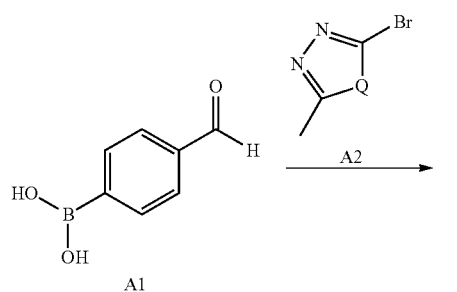

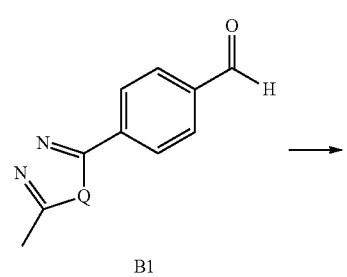

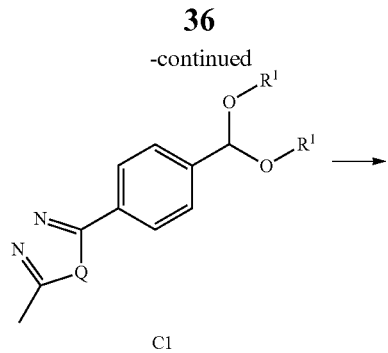

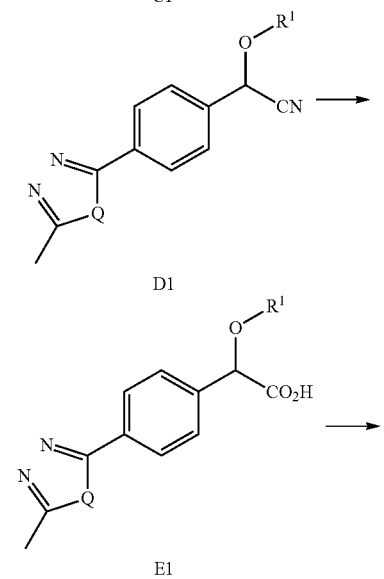

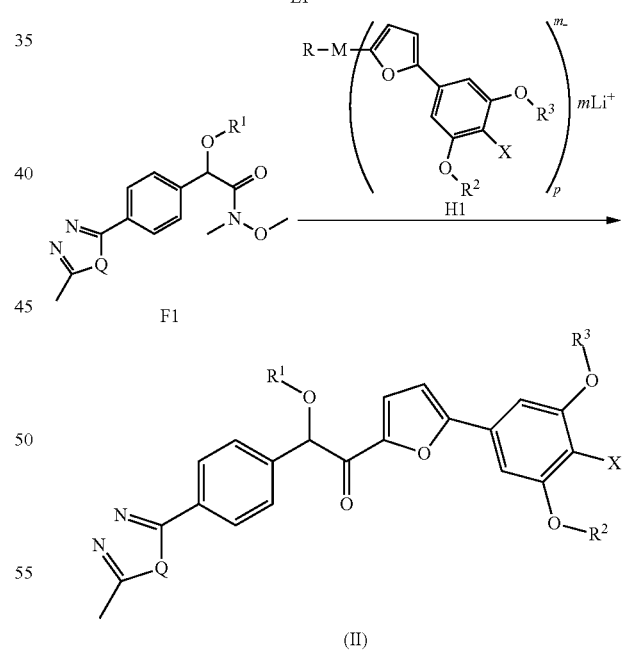

which process comprises:
converting boronic acid A1 to carbaldehyde B1 through activation of the boronic acid with an activating reactant A2;
converting carbaldehyde B1 to acetal C1 under acid catalysis with a suitable source of orthoformate;
converting acetal C1 to nitrile D1 through catalyzed cyanation with a metal catalyst and a cyanide source;

hydrolyzing D1 with a suitable acid to give carboxylic acid E1;

converting carboxylic acid E1 to amide F1 with a suitable base, a suitable coupling reagent, and a source amine;

converting amide F1 to a compound of Formula (II) with an anionic coupling reagent having structure H1, wherein M is a Group I metal, a Group II metal, Cu, or Zn;

R, $R^2$, and $R^3$ are each independently $C_{(1-6)}$alkyl;

m is 1, 2, 3, or 4;

p is 1, 2, 3, or 4; and optionally converting the compound of Formula (II) to a salt.

2. The process of claim 1, wherein Q is O.
3. The process of claim 1, wherein Q is S.
4. The process of claim 1, wherein X is Cl.
5. The process of claim 1, wherein X is Br.
6. The process of claim 1, wherein M is a Group II metal.
7. The process of claim 1, wherein M is Mg.
8. The process of claim 1, wherein $R^1$ is methyl, ethyl or propyl.
9. The process of claim 1, wherein $R^1$ is ethyl.
10. The process of claim 1, wherein $R^2$ is methyl, ethyl or propyl.
11. The process of claim 1, wherein $R^2$ is methyl.
12. The process of claim 1, wherein $R^3$ is methyl, ethyl or propyl.
13. The process of claim 1, wherein $R^3$ is methyl.
14. The process of claim 1, wherein R is butyl.
15. The process of claim 1, wherein the acid catalyst used to create acetal C1 is para-toluenesulfonic acid monohydrate.
16. The process of claim 1, wherein the suitable source of orthoformate is triethyl orthoformate.
17. The process of claim 1, wherein the metal catalyst of the cyanation step is a cobalt salt.
18. The process of claim 1, wherein the metal catalyst of the cyanation step is $CoCl_2$.
19. The process of claim 1, wherein the cyanide source is trimethylsilyl cyanide.
20. The process of claim 1, wherein the suitable acid of the hydrolysis step is HCl.
21. The process of claim 1, wherein the suitable base of the amidation step is triethylamine.
22. The process of claim 1, wherein the suitable coupling reagent of the amidation step is propylphosphonic anhydride.
23. The process of claim 1, wherein the source amine is N,O-dimethylhydroxylamine hydrochloride.
24. The process of claim 1, wherein the compound of Formula (II) is:

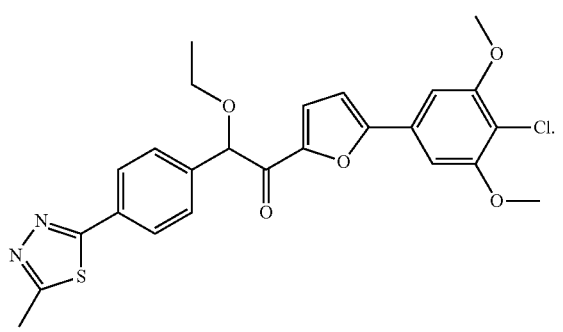

25. The process of claim 1, wherein the compound of Formula (II) is:

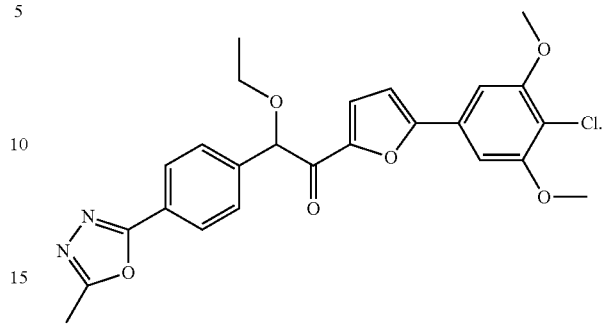

26. The process of claim 1, wherein the compound of Formula (II) is:

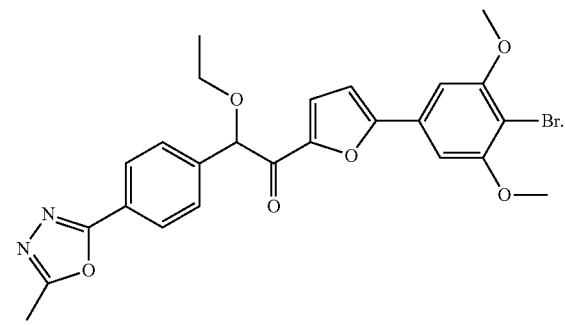

27. A process to prepare a compound of Formula H1:

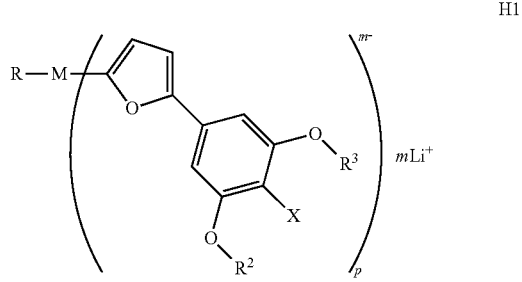

wherein

M is a Group I metal, a Group II metal, Cu, or Zn,

R, $R^2$ and $R^3$ are each independently $C_{(1-6)}$alkyl,

X is Cl or Br, m is 1, 2, 3, or 4, and p is 1, 2, 3, or 4;

according to the following General Scheme (II):

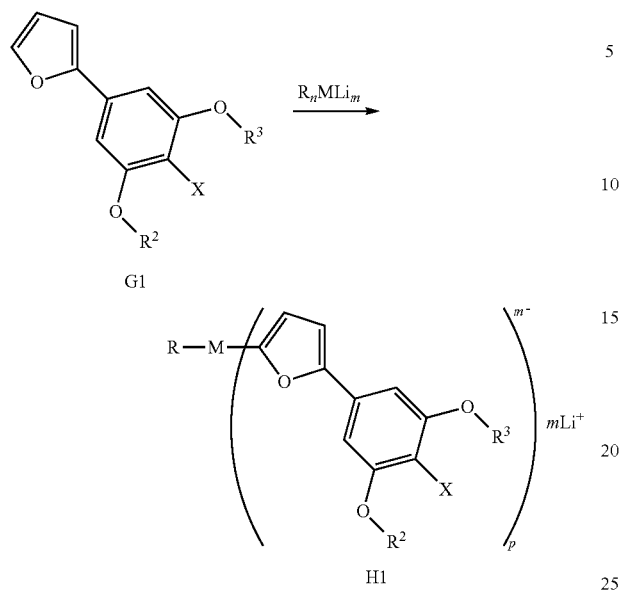

which process comprises:
preparing in a solvent solution a lithium alkyl metal base from $R_n$—Li and a metal halide comprising M, wherein n is 1, 2, 3 4, or 5; and
preparing a mixed metal lithiate H1 from G1 and the lithium alkyl metal base.

28. The process of claim 27, wherein $R^2$ is methyl, ethyl, or propyl.

29. The process of claim 27, wherein $R^2$ is methyl.

30. The process of claim 27, wherein $R^3$ is methyl, ethyl, or propyl.

31. The process of claim 27, wherein $R^3$ is methyl.

32. The process of claim 27, wherein R is butyl.

33. The process of claim 27, wherein X is Cl.

34. The process of claim 27, wherein X is Br.

35. The process of claim 27, wherein M is a Group II metal.

36. The process of claim 27, wherein M is Mg.

37. The process of claim 27, wherein the lithium alkyl metal base is a lithium alkylmagnesate base.

38. The process of claim 27, wherein the lithium alkyl metal base is $Bu_4MgLi_2$.

39. The process of claim 27, wherein the compound of Formula H1 is:

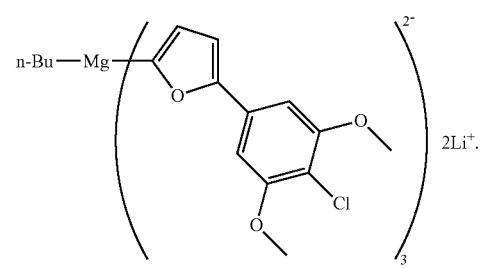

40. A process to prepare a compound of Formula (III):

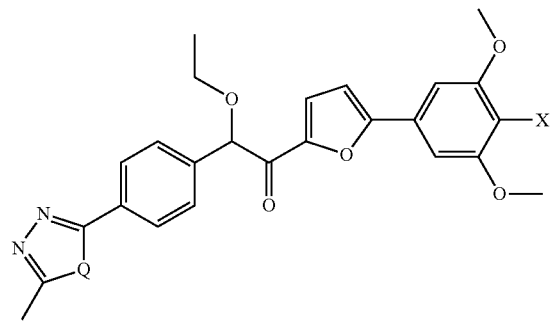

wherein Q is S or O and X is Cl or Br,
according to the following General Scheme (III):

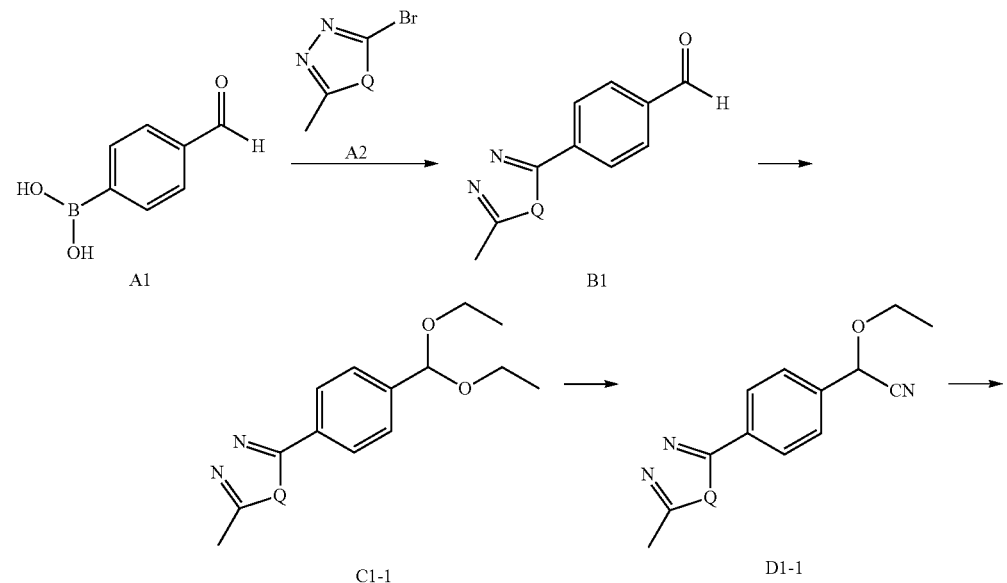

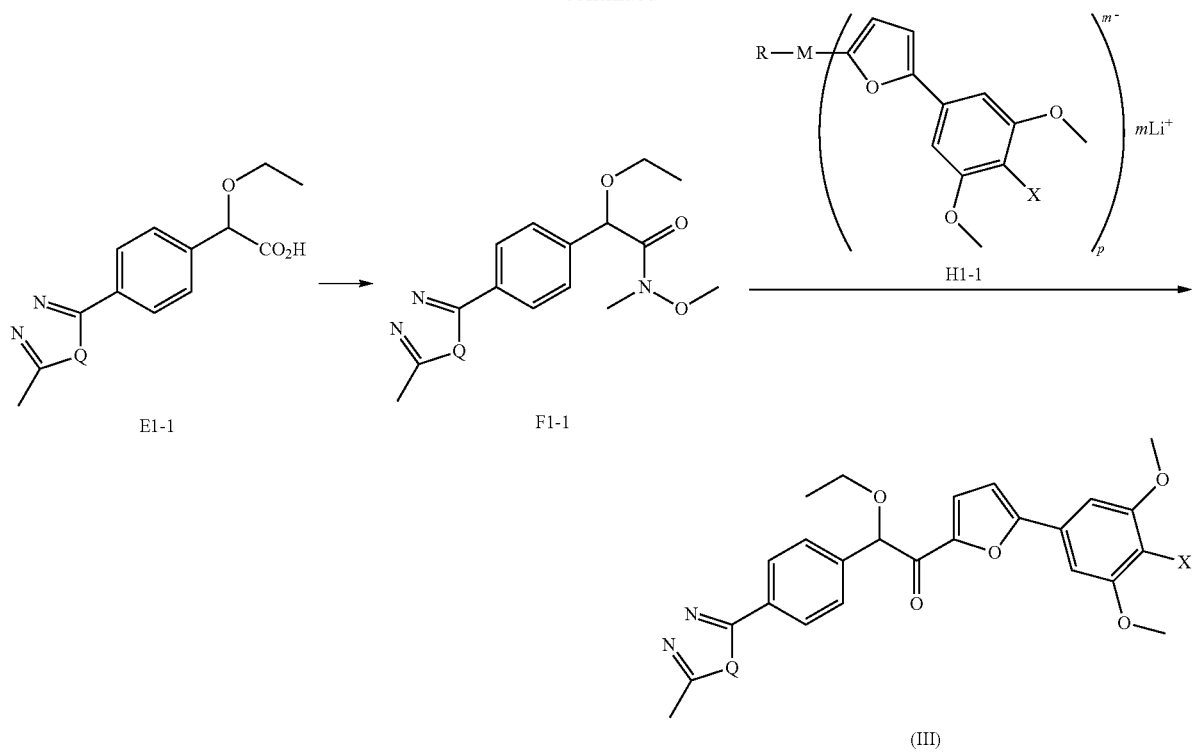

which process comprises:
  converting boronic acid A1 to carbaldehyde B1 through activation of the boronic acid with an activating reactant A2;
  converting carbaldehyde B1 to acetal C1-1 under acid catalysis with a suitable source of orthoformate;
  converting acetal C1-1 to nitrile D1-1 through catalyzed cyanation with a metal catalyst and a cyanide source;
  hydrolyzing D1-1 with a suitable acid to give carboxylic acid E1-1;
  converting carboxylic acid E1-1 to amide F1-1 with a suitable base, a suitable coupling reagent, and a source amine;
  converting amide F1-1 to a compound of Formula (III) with an anionic coupling reagent having structure H1-1,
  wherein
    M is a Group I metal, a Group II metal, Cu, or Zn;
    R is $C_{(1-6)}$alkyl;
    m is 1, 2, 3, or 4;
    p is 1, 2, 3, or 4; and
  optionally converting the compound of Formula (III) to a salt.

41. The process of claim 40, wherein Q is O.
42. The process of claim 40, wherein Q is S.
43. The process of claim 40, wherein X is Cl.
44. The process of claim 40, wherein X is Br.
45. The process of claim 40, wherein M is a Group II metal.
46. The process of claim 40, wherein M is Mg.
47. The process of claim 40, wherein R is butyl.
48. The process of claim 40, wherein the acid catalyst used to create acetal C1-1 is para-toluenesulfonic acid monohydrate.
49. The process of claim 40, wherein the suitable source orthoformate is triethyl orthoformate.
50. The process of claim 40, wherein the metal catalyst of the cyanation step is a cobalt salt.
51. The process of claim 40, wherein the metal catalyst of the cyanation step is $CoCl_2$.
52. The process of claim 40, wherein the cyanide source is trimethylsilyl cyanide.
53. The process of claim 40, wherein the suitable acid of the hydrolysis step is HCl.
54. The process of claim 40, wherein the suitable base of the amidation step is trietylamine.
55. The process of claim 40, wherein the suitable coupling reagent of the amidation step is propylphosphonic anhydride.
56. The process of claim 40, wherein the source amine is N,O-dimethylhydroxylamine hydrochloride.
57. The process of claim 40, wherein the compound of Formula (III) is:

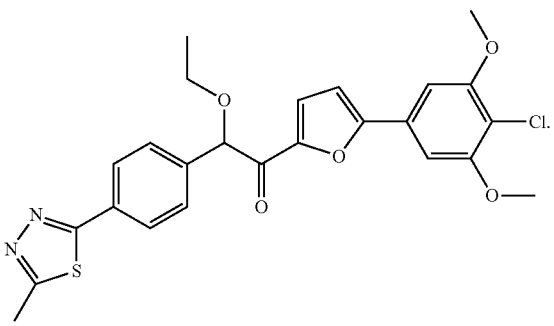

58. The process of claim 40, wherein the compound of Formula (III) is:

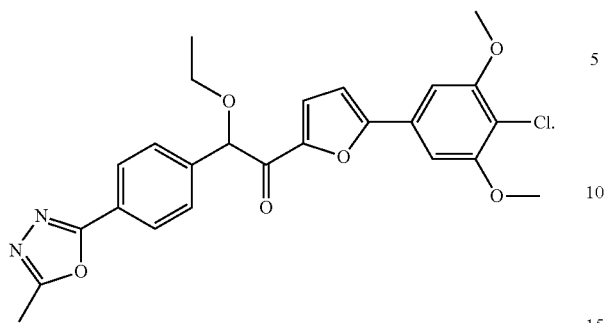

59. The process of claim 40, wherein the compound of Formula (III) is:

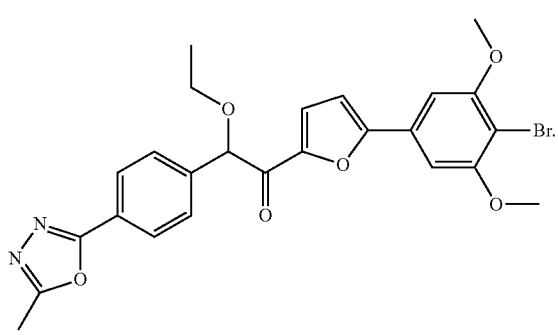

60. A process to prepare a compound of Formula H1-1:

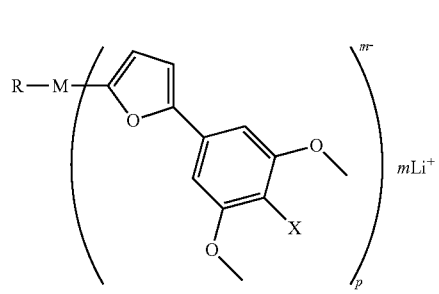

wherein
M is a Group I metal, a Group II metal, Cu, or Zn,
R is $C_{(1-6)}$alkyl,
X is Cl or Br,
m is 1, 2, 3, or 4, and
p is 1, 2, 3, or 4;
according to the following General Scheme (IV):

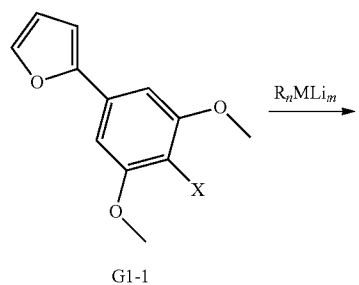

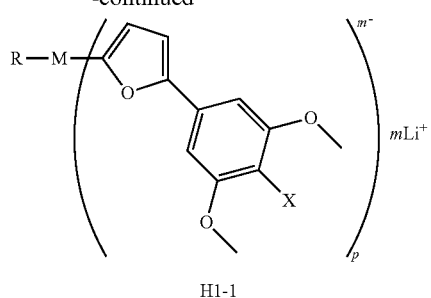

which process comprises:
preparing in a solvent solution a lithium alkyl metal base from $R_n$—Li and a metal halide comprising M, wherein n is 1, 2, 3 4, or 5; and
preparing a mixed metal lithiate H1-1 from G1-1 and the lithium alkyl metal base.

61. The process of claim 60, wherein X is Cl.

62. The process of claim 60, wherein X is Br.

63. The process of claim 60, wherein M is a Group II metal.

64. The process of claim 60, wherein M is Mg.

65. The process of claim 60, wherein R is butyl.

66. The process of claim 60, wherein the lithium alkyl metal base is a lithium alkylmagnesate base.

67. The process of claim 60, wherein the lithium alkyl metal base is $Bu_4MgLi_2$.

68. The process of claim 60, wherein the compound of Formula H1-1 is:

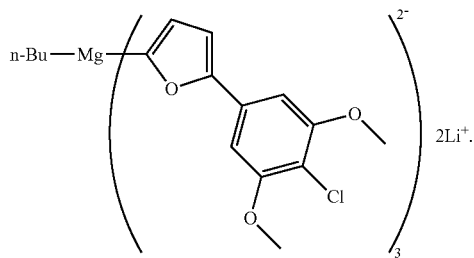

69. A compound having the structure of Formula H1:

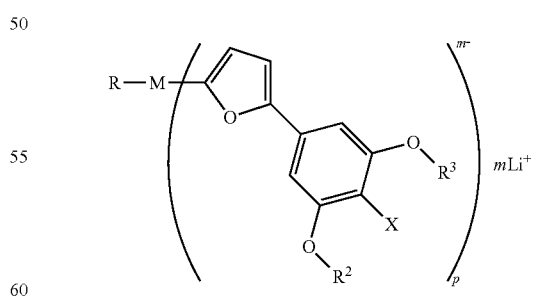

wherein
M is a Group I metal, a Group II metal, Cu, or Zn,
R, $R^2$, and $R^3$ are each independently $C_{(1-6)}$alkyl,
X is Cl or Br,
m is 1, 2, 3, or 4, and
p is 1, 2, 3, or 4.

70. The compound of claim 69 having the structure of Formula H1-1:

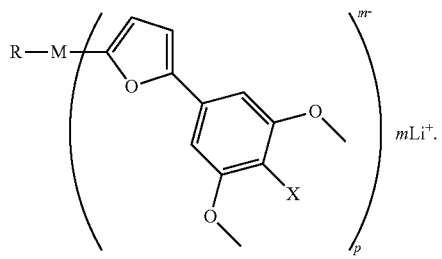

71. The compound of claim 69, wherein M is magnesium.

72. The compound of claim 69 having the structure of Formula H1-1a:

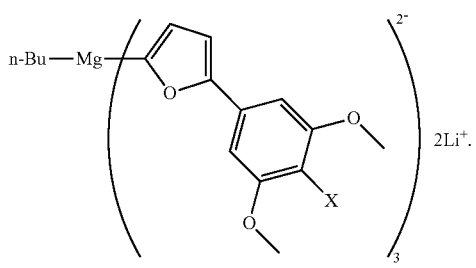

73. The compound of claim 69, wherein X is Cl.

74. The compound of claim 69, wherein X is Br.

75. The compound of claim 69, having the following structure:

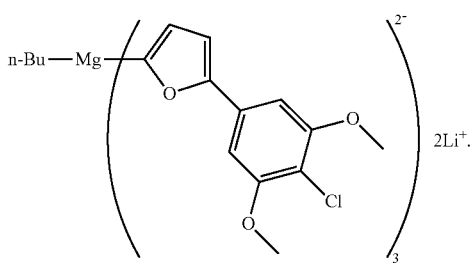

76. A compound having the following structure:

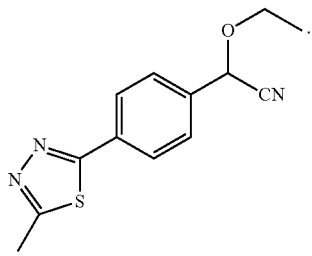 [SMILES: CCOC(C#N)c1ccc(-c2nnc(C)s2)cc1]

77. A compound having the following structure:

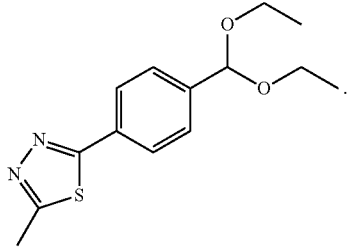 [SMILES: CCOC(OCC)c1ccc(-c2nnc(C)s2)cc1]

* * * * *

UNITED STATES PATENT AND TRADEMARK OFFICE
CERTIFICATE OF CORRECTION

Page 1 of 5

PATENT NO.           : 9,650,368 B2
APPLICATION NO.      : 14/696287
DATED                : May 16, 2017
INVENTOR(S)          : Neil S. Cutshall et al.

It is certified that error appears in the above-identified patent and that said Letters Patent is hereby corrected as shown below:

In the Specification

| Column | Line | Error |
|---|---|---|
| 3 | 26 | Replace the compounds of General Scheme (I) with the following: |

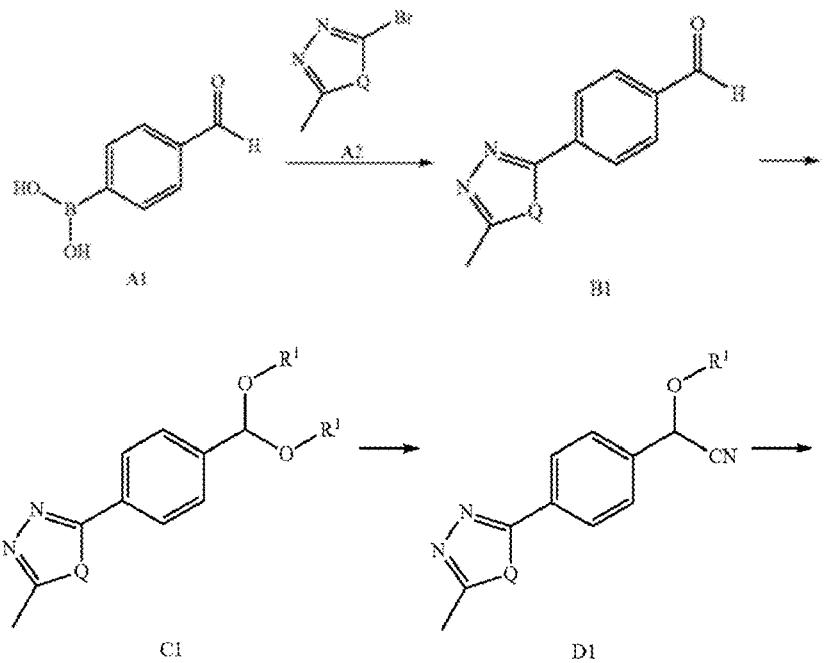

Signed and Sealed this
Twenty-sixth Day of December, 2017

Joseph Matal
*Performing the Functions and Duties of the
Under Secretary of Commerce for Intellectual Property and
Director of the United States Patent and Trademark Office*

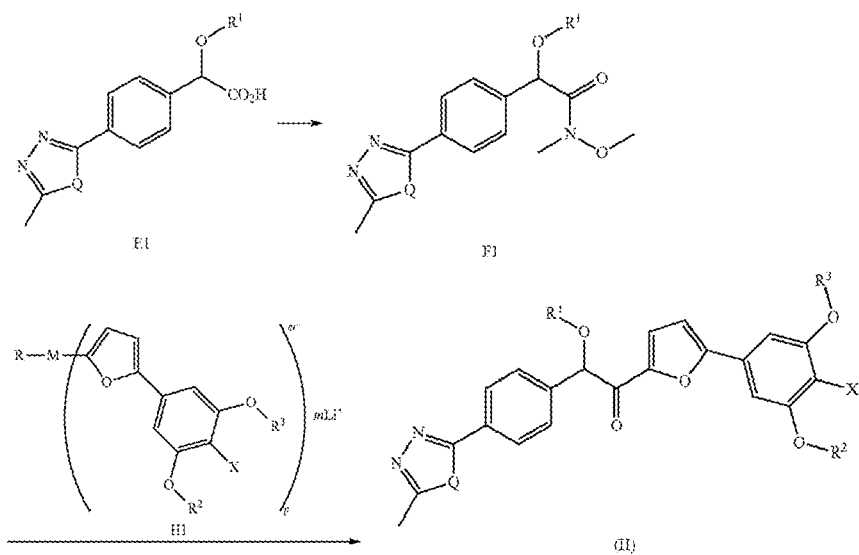
| 7 | 2 | Replace the compounds of General Scheme (III) with the following: |
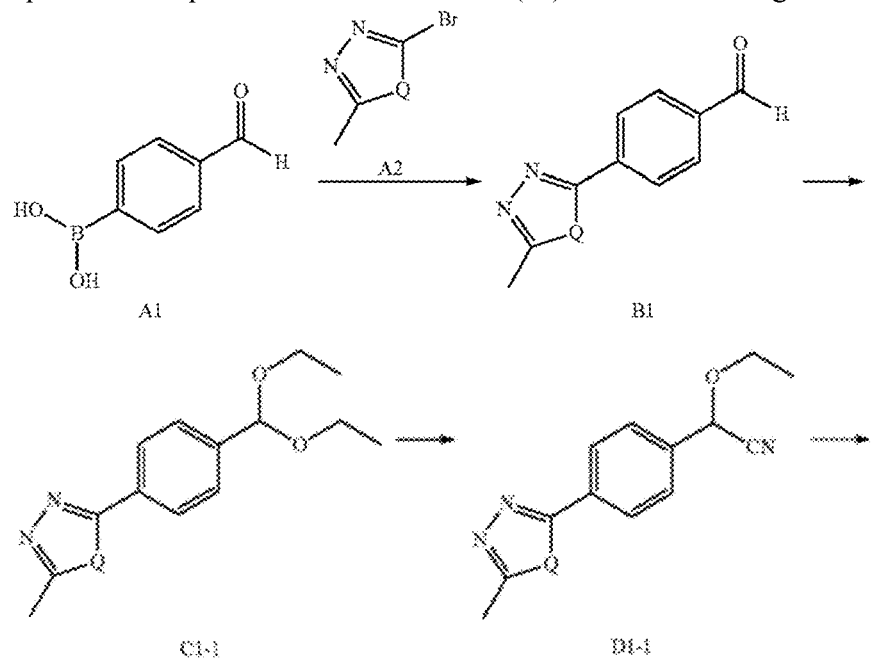

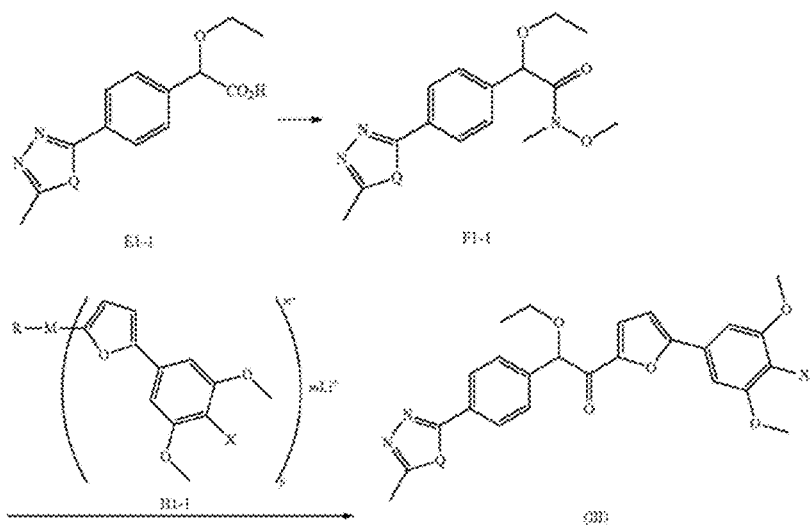
35 42 Replace the compounds of General Scheme (I) with the following:
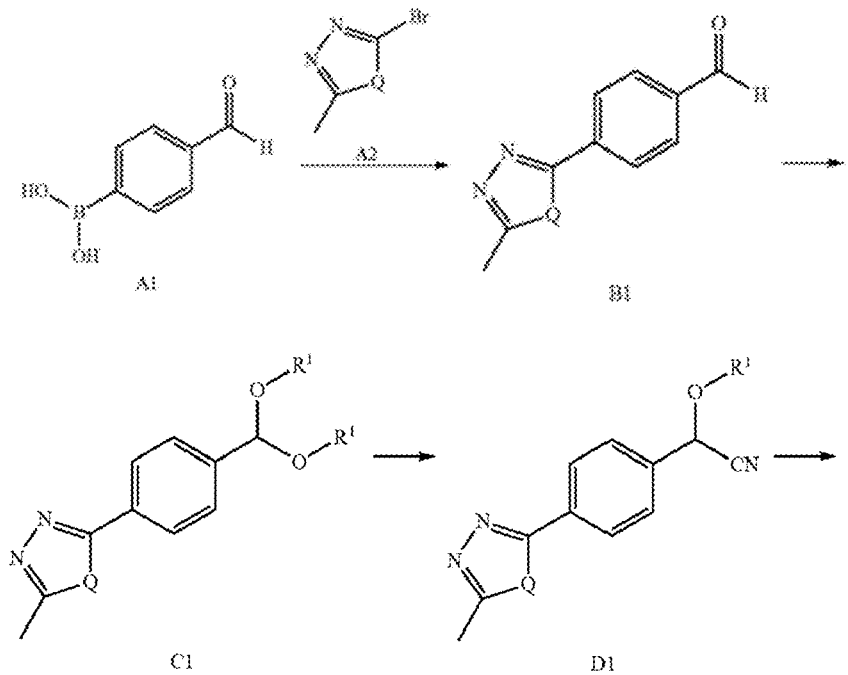

CERTIFICATE OF CORRECTION (continued)
U.S. Pat. No. 9,650,368 B2

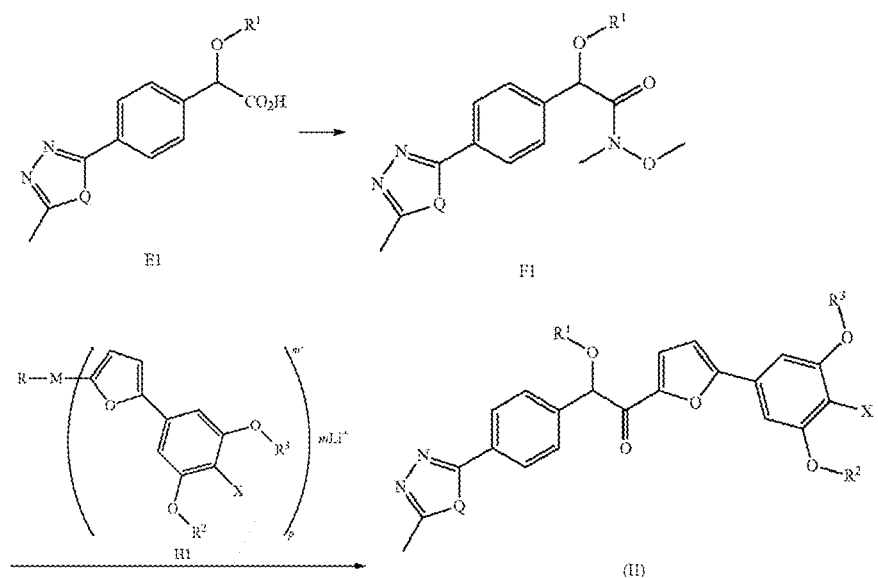

| 39 | 43 | Replace the compounds of General Scheme (III) with the following: |

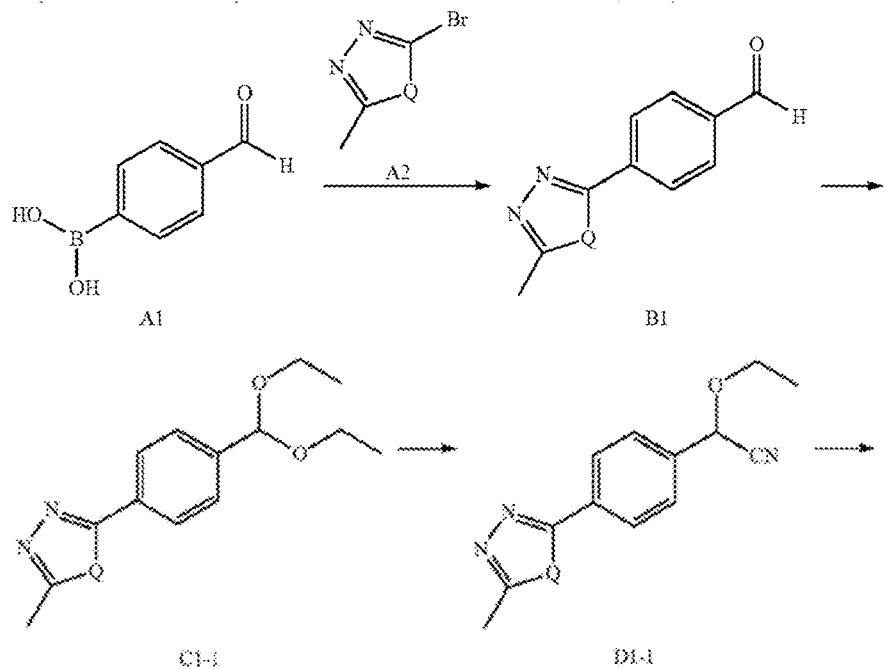

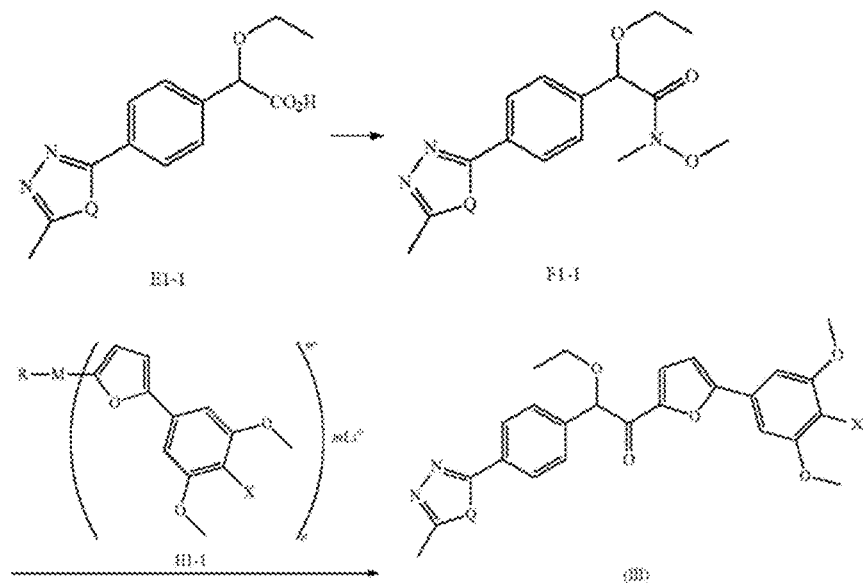
| 42 | 44 | "trietylamine" should read --triethylamine-- |